United States Patent
Knowlton et al.

(10) Patent No.: US 11,385,235 B2
(45) Date of Patent: Jul. 12, 2022

(54) DNA INK—NEAR-FIELD ABSORPTION COUPLING FOR COLORIMETRIC DETECTION, DNA INK, CHROMIC PHOTOSWITCHES, AND CHROMIC MOLECULAR RULER

(71) Applicant: Boise State University, Boise, ID (US)

(72) Inventors: William B. Knowlton, Boise, ID (US); Bernard Yurke, Boise, ID (US); Brittany Cannon, Boise, ID (US); Elton Graugnard, Boise, ID (US)

(73) Assignee: Boise State University, Boise, ID (US)

( * ) Notice: Subject to any disclaimer, the term of this patent is extended or adjusted under 35 U.S.C. 154(b) by 90 days.

(21) Appl. No.: 16/059,954

(22) Filed: Aug. 9, 2018

(65) Prior Publication Data
US 2019/0101543 A1  Apr. 4, 2019

Related U.S. Application Data

(60) Provisional application No. 62/543,078, filed on Aug. 9, 2017.

(51) Int. Cl.
| | |
|---|---|
| G01N 33/58 | (2006.01) |
| G01N 21/64 | (2006.01) |
| C12Q 1/6816 | (2018.01) |
| G01N 33/542 | (2006.01) |
| C09K 11/07 | (2006.01) |

(52) U.S. Cl.
CPC ........... *G01N 33/582* (2013.01); *C09K 11/07* (2013.01); *C12Q 1/6816* (2013.01); *G01N 21/6428* (2013.01); *G01N 33/542* (2013.01); *C09K 2211/1029* (2013.01); *G01N 2021/6441* (2013.01)

(58) Field of Classification Search
CPC ............................. G01N 33/582; C12Q 1/6816
See application file for complete search history.

(56) References Cited

U.S. PATENT DOCUMENTS

| | | | |
|---|---|---|---|
| 9,073,962 B2 | 7/2015 | Fracchia et al. | |
| 2015/0218204 A1 | 8/2015 | Yin et al. | |
| 2017/0190573 A1 | 7/2017 | Shen et al. | |
| 2018/0044372 A1 | 2/2018 | Han et al. | |

FOREIGN PATENT DOCUMENTS

WO      2014018675 A1    1/2014

OTHER PUBLICATIONS

Ma et al ,Rapid and enzyme-free nucleic acid detection based on exponential hairpin assembly in complex biological fluids, 2016, Analyst, 141, 2883-2886 (Year: 2016).*
Ma et al ,Rapid and enzyme-free nucleic acid detection based on exponential hairpin assembly in complex biological fluids, 2016, Analyst, 141, 2883-2886 supplemental information, pp. 1-9 (Year: 2016).*
Chen et al, Self-assembled DNA tetrahedral optofluidic lasers with precise and tunable gain control, 2013, Lab Chip, 13, 3351-3354 (Year: 2013).*
Chen et al, Self-assembled DNA tetrahedral optofluidic lasers with precise and tunable gain control, 2013, Lab Chip, 13, 3351-3354 Supplemental information, pp. 1-2 (Year: 2013).*
Lee et al., Dynamics of Nucleosome Assembly and Effects of DNA Methylation, 2014, The Journal of Biological Chemistry, 290, pp. 4291-4303 (Year: 2014).*
Kato et al., Development of a Robust Model System of FRET using Base Surrogates Tethering Fluorophores for Strict Control of Their Position and Orientation within DNA Duplex, 2013, J. Am. Chem. Soc., 135, 741-750 (Year: 2013).*
Markova et al, J- vs. H-type assembly: pentamethine cyanine (Cy5) as a near-IR chiroptical reporter, 2013, Chem. Commun., 49, 5298-5300. (Year: 2013).*
Barrois et al, The role of duplex stability for wavelength-shifting fluorescent DNA probes: energy transfer vs. exciton interactions in DNA traffic lights, 2014, Photochem. Photobiol. Sci., 13, 1126-1129. (Year: 2014).*
Cannon et al., "Coherent Exciton Delocalization in a Two-State DNA-Templated Dye Aggregate System", Journal of Physical Chemistry, vol. 121, pp. 6905-6916, Aug. 16, 2017.
Cannon et al., "Large Davydov Splitting and Strong Fluorescence Suppression: An Investigation of Exciton Delocalization in DNA-Templated Holliday Junction Dye Aggregates", Journal of Physical Chemistry, vol. 122, pp. 2086-2095, Feb. 8, 2018.
Cannon et al., "Large Davydov Splitting and Strong Fluorescence Suppression: An Investigation of Exciton Delocalization in DNA-Templated Holliday Junction Dye Aggregates", Supporting Information, 20 pages, Feb. 8, 2018.
Childs et al., "Universal Computation by Multiparticle Quantum Walk", Science Mag., vol. 339, pp. 791-794, Feb. 15, 2013.
Graugnard et al., "DNA-Controlled Excitonic Switches", NANO Letters, vol. 12, pp. 2117-2122, Mar. 8, 2012.
Hannestad et al., "Self-Assembled DNA-Based Fluorescence Waveguide with Selectable Output", Nanotechnology, vol. 22, pp. 3178-3185, 2011.
Ke et al., "Three-Dimensional Structures Self-Assembled from DNA Bricks", Science, vol. 338(6111), 16 pages, Nov. 30, 2012.

(Continued)

*Primary Examiner* — Narayan K Bhat
(74) *Attorney, Agent, or Firm* — McKee, Voorhees & Sease, PLC

(57) ABSTRACT

The nucleotides can then be polymerized into oligomers. The design of the oligomers will depend on the design of the overall architecture. Simple architectures may be designed by any methods. However, more complex architectures may be design using software, such as caDNAno (as described at cadnano.org/docs.html, and herein incorporated by reference), to minimize errors and time. The user may input the desired shape of the architecture into the software and once finalized, the software will provide the oligomer sequences of the bricks to create the desired architecture. The length of the oligomers may be from about 10 to about 10,000, or less than about 9,000, less than about 8,000, less than about 5,000 nucleotides in length. The length of the oligomer will be optimized for the type of architecture used.

18 Claims, 19 Drawing Sheets

(56) References Cited

OTHER PUBLICATIONS

Stein et al., "Single-Molecule Four-Color FRET Visualizes Energy-Transfer Paths on DNA Origami", Journal of American Chemical Society, vol. 133, pp. 4193-4195, Jan. 20, 2011.
Wei et al., "Complex shapes self-assembled from single-stranded DNA tiles", Nature, vol. 485, pp. 623-627, May 31, 2012.
Yurke et al., "Passive linear nanoscale optical and molecular electronics device synthesis from nanoparticles", Physical Review, vol. A81, 9 pages, 2010.
Zhang et al., "Engineering Entropy-Driven Reactions and Networks Catalyzed by DNA", Science, vol. 318, pp. 7 pages, Nov. 16, 2007.

* cited by examiner

DNA INK—NEAR-FIELD ABSORPTION COUPLING FOR COLORIMETRIC DETECTION, DNA INK, CHROMIC PHOTOSWITCHES, AND CHROMIC MOLECULAR RULER

CROSS REFERENCE TO RELATED APPLICATION

The present application claims priority to the earlier filed U.S. Provisional Application having Ser. No. 62/543,078, filed Aug. 9, 2017, and hereby incorporates subject matter of the provisional application in its entirety.

GRANT REFERENCE

This invention was made with government support under Grant No. NNX15AI04H, awarded by the National Aeronautics and Space Administration, Grant No. ECCS-1014922, awarded by the National Science Foundation (NSF), Grant No. ECCS-1648655, awarded by the National Science Foundation (NSF), and Grant No. P20 RR016454, awarded by the National Institute of Health. The Government has certain rights in the invention.

FIELD OF THE INVENTION

The invention relates generally to near-field absorption coupling. More specifically, the invention pertains to colorimetric detection, DNA ink, chromic photoswitches, and chromic molecular rulers.

BACKGROUND OF THE INVENTION

DNA nanotechnology has been used to create a variety of one-, two-, and three-dimensional architectures resulting in unprecedented control of both the placement and spacing of nanoparticles, such as chromophores, quantum dots, and gold nanoparticles. Because of the self-assembly properties of nucleotides, design and development of new biomimetic, bioinspired, and bioenabled materials with relatively inexpensive processing steps holds tremendous potential for a wide variety of industries. This pioneering field has led to the creation of new bioenabled and biohybrid materials that self-assemble with a wide range of applications from nanophotonic waveguides to colorimetric detection to artificial photosynthetic light-harvesting antennae. These new materials provide excellent opportunities to study fundamental and emergent physical properties.

When chromophores self-aggregate, a variety of quantum effects have been observed including Davydov splitting, Dicke superradiance, excitonic quantum coherence, superquenching, exchange narrowing, fluorescence-phosphorescence mixing, and circular dichroism. Aggregates have been identified as a possible option for organic solar cells because they have much longer diffusion lengths than the other alternative, organic bulk heterojunctions which evidently have few material options. Aggregates are classified as either J- or H-aggregates, dimers, or types with each displaying intriguing excitonic properties. These properties are the result of their ability to form molecular excitons otherwise known as Frenkel excitons. A Frenkel or molecular exciton is a chromophore exited state that is delocalized over a number of spatially separated chromophores—the superposition of molecule-localized transition densities—yet electron density remains localized on the individual molecules. Quantum coherent excitonic behaviors is indicated by the delocalization of the molecular exciton. Most earlier studies examining aggregate exciton behavior employed homogeneous nucleation in which the solution is supersaturated with chromophores, including self-assembled aggregation.

To promote chromophore aggregation, heterogeneous nucleation is used in which macromolecular templates were implemented to facilitate chromophore aggregation. The macromolecular templates include polypeptides, polysaccharides, semiconductive polymers, and DNA. One-dimensional DNA duplexes have been used to heterogeneously aggregate high concentrations of free chromophores that intercalate in the minor groove of certain base sequences through secondary bonding via electrostatic and dipolar forces. Resulting optical properties suggest the mixed presence of J- and H-dimers, aggregates, and their monomers. The structure of the aggregates has been controversial because it is difficult to resolve molecular packing details. Both the mixed presence of different aggregates and the difficulty of resolving aggregate structure indicates insufficient control over aggregation position and geometry.

Naturally occurring molecular aggregates in biocomposite structures are readily observe in plant-based light harvesting systems. Several chromophore-protein scaffold self-assemblies in which chromophores are bound to the protein scaffold, exhibit some evidence of excitonic quantum coherence. Recent research in this area has generated significant interest from the quantum computing community. This interest has yielded new physical insights in environmentally assisted quantum transport. Consequently, environmental influences need not necessarily immediately degrade quantum coherence.

It is clear that the impact of successfully mimicking natural photosynthetic systems by developing artificial or bio-hybrid nanophotonic systems would be substantial. Protein self-assembly and large covalent molecular array synthesis are approaches used to assemble artificial photosynthetic systems from functional modular building blocks. The former approach is limited by the complexity of protein folding as a fundamental understanding of the process that continues to evade researchers, while the later approach is evidently formidable, inefficient, and costly. Self-assembled active modular components are a third alternative, which will elf order into artificial excitonic systems; however, it has met with limited success. To circumvent the inherent limitations of these approaches, nucleotide nanotechnology offers a powerful means to control the geometry and dimensionality of a chromophore aggregate to form excitonic systems. Materials with specific excitonic properties can be designed and fabricated enabling the investigation of fundamental molecular level mechanisms and phenomena. Control of the chromophore placement promotes novel biomaterials development and offer new paradigms toward quantum information processing.

BRIEF SUMMARY OF THE INVENTION

Applicants have created compositions of one or more chromophores attached to a nucleotide architecture. When two or more chromophores are held within the nucleotide architecture, they are spaced sufficiently close enough together such that near-field interactions (nanospaced), such as but not limited to electromagnetic dipole-dipole interactions or orbital overlap, form and result in a change in absorption of wavelengths.

In an embodiment, the change in absorption may be measured by absorbance. In another embodiment the change in absorption is large enough that the difference may be measured by visual observation with the unaided eye for machine-free obtainable results.

In some embodiments, the chromophores bound to a nucleotide oligomer may be used in a colorimetric detection system or circuit in a sample to detect the complement strand in a sample for the detection of genomic diseases, biolabeling, or for medical diagnostics. In other embodiment, the colorimetric detection system uses a targeting molecule to detect chemicals or proteins within a sample for medical diagnostics or for aptamer readout in various fields, such as agriculture, veterinary, and biological sciences.

In another embodiment, an ink may comprise a water-soluble solution of the chromophores and nucleotide architecture. In a further embodiment, a second ink may be used to change the absorbance spectrum of both inks to produce a color change. In a further embodiment, any printer capable of dispensing aqueous solutions may be used to print colorimetric arrays for the detection and identification of various compounds such as, but not limited to, volatile organic compounds, vapor-phased molecules, and small molecules such as, but not limited to, ammonium, nitrates, and carbon species.

In another embodiment, the near-field interactions between chromophores may induce a sufficient change in the electronic structure to be used as a chromic photoswitch. In some embodiments, quenching or superquenching may be used to create the on/off states. In other embodiments, nucleic acid strand invasion may be used to change the absorbance spectrum of the active dye. In one embodiment, the photoswitches may be incorporated in bioinspired synthetic photosynthetic systems as photoprotective agents and/or for self-repair capabilities that are currently only found in nature. In another embodiment, they may also be incorporated into dye sensitized photovoltaics or solar cells in which two chromophores incorporated rather than one dye if the incoming light is better suited for chromophore than the other chromophore. In a further embodiment the active dye can be changed via nucleotide strand invasion.

In another embodiment two or more sufficiently close chromophores are used as a chromic molecular ruler. The near-field coupling between two or more chromophores which are sufficiently close change the energy band structure allowing the chromophores to act as a single chromophore allowing them to work at closer distances and with more sensitivity than traditional fluorescence resonance energy transfer (FRET).

In the embodiments, the nucleotide architecture is self-assembling. In yet other embodiment, the nucleotide architecture is single stranded. In another embodiment, to allow the attachment of additional chromophores when compared to a single stranded architecture, the nucleotide architecture is double stranded. In some embodiments the nucleotide architecture is linear for fast transmission speed down a wire or to allow fine tuning by reagents. In other embodiments, the nucleotide architecture is two- or three-dimensional to allow for more complex circuits or to increase rigidity of the chromophores within the architecture. In other embodiments, the nucleotide strands comprising the architecture may be branched to allow for increased complexity of the structure. In further embodiments, the nucleotide strands are configured by nucleotide origami. In other further embodiments, the nucleotide strands are configured into nucleotide bricks allowing for very complex and controlled three-dimensional structures.

While multiple embodiments are disclosed, still other embodiments of the present invention will become apparent to those skilled in the art from the following detailed descriptions, which show and describe illustrative embodiments of the invention. Accordingly, the figures and detailed description are to be regarded as illustrative in nature and not restrictive.

BRIEF DESCRIPTION OF THE DRAWINGS

FIGS. 1A-1C show the chromophore bound to the same nucleotide duplex.

DETAILED DESCRIPTION

Figure 1A:
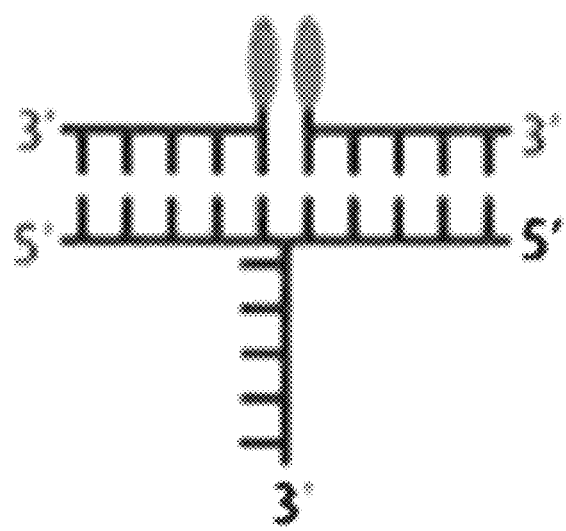
FIG. 1A is a schematic representation of a simple three-way branched nucleotide brick bringing together two other bricks with the chromophore bound to their 5' ends.

Unless otherwise defined herein, scientific and technical terms used in connection with the invention shall have the meanings that are commonly understood by those of ordinary skill in the art. Further, unless otherwise required by context, singular terms shall include the plural and plural terms shall include the singular. Generally, nomenclatures used in connection with, and techniques of, biochemistry, enzymology, molecular and cellular biology, microbiology, genetics and protein and nucleic acid chemistry and hybridization described herein are those well-known and commonly used in the art. The methods and techniques are generally performed according to conventional methods well known in the art and as described in various general and more specific references that are cited and discussed throughout the present specification unless otherwise indicated.

Definitions

The following terms, unless otherwise indicated, shall be understood to have the following meanings:

It should be noted that, as used in this specification and the appended claims, the singular forms "a," "an," and "the" include plural referents unless the content clearly dictates otherwise. Thus, for example, reference to a composition containing "a compound" includes a mixture of two or more compounds. It should also be noted that the term "or" is generally employed in its sense including "and/or" unless the content clearly dictates otherwise.

Numeric ranges recited within the specification are inclusive of the numbers defining the range and include each integer within the defined range. Throughout this disclosure, various aspects of this invention are presented in a range format. It should be understood that the description in range format is merely for convenience and brevity and should not be construed as an inflexible limitation on the scope of the invention. Accordingly, the description of a range should be considered to have specifically disclosed all the possible sub-ranges, fractions, and individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6, and decimals and fractions, for example, 1.2, 3.8, 1½, and 4¾ This applies regardless of the breadth of the range.

Other than in the operating examples, or where otherwise indicated, all numbers expressing quantities of ingredients or reaction conditions used herein are to be understood as being modified in all instances by the term "about".

As used herein, the term "about" modifying the quantity of an ingredient in the compositions of the invention or employed in the methods of the invention refers to variation in the numerical quantity that can occur, for example, through typical measuring and liquid handling procedures used for making concentrates or use solutions in the real world; through inadvertent error in these procedures; through differences in the manufacture, source, or purity of the ingredients employed to make the compositions or carry out the methods; and the like. The term about also encompasses amounts that differ due to different equilibrium conditions for a composition resulting from a particular initial mixture. Whether or not modified by the term "about," the claims include equivalents to the quantities.

"Non-covalent" refers to any molecular interactions that are not covalent—i.e. the interaction does not involve the sharing of electrons. The term includes, for example, electrostatic, π-effects, van der Waals forces, and hydrophobic effects. "Covalent" refers to interactions involving the sharing of one or more electrons.

As used herein, a "nucleotide" is any nucleoside linked to a phosphate group. The nucleoside may be natural, including but not limited to, any of cytidine, uridine, adenosine, guanosine, thymidine, inosine (hypoxanthine), or uric acid; or synthetic, including but not limited to methyl-substituted phenol analogs, hydrophobic base analogs, purine/pyrimidine mimics, icoC, isoG, thymidine analogs, fluorescent base analogs, or X or Y synthetic bases. Alternatively, a nucleotide may be abasic, such as but not limited to 3-hydroxy-2-hydroxymethyl-tetrahydrofuran, which act as a linker group lacking a base or be a nucleotide analog. As used herein, nucleotide is used interchangeably with "nucleic acid."

As used herein, "nucleotide duplex" is when two strands of complement nucleotide oligomers complementary bind to each other. The two strands may be part of the same nucleotide molecule or separate nucleotide molecules.

As used herein, a "nucleotide brick" or "brick" is an oligomer or strand of nucleotides that may form with itself and/or other bricks or strands into one-, two-, or three-dimensional "structures" or "architectures." As used herein, the terms "oligomer" and "strand" are used interchangeably.

As used herein, "nucleotide origami" is an architecture comprising of two or more nucleotide bricks, where one brick is a "scaffold" and provides the main body of the overall structure and is bound by one or more "staple(s)."

As used herein, a "scaffold" is a single stranded nucleotide brick rationally-designed to self-assemble into hairpin loops, helical domains, and locking domains. The scaffold may use staples to direct the folding and to hold the final shape. Alternatively, the scaffold may use intrinsic self-complementary pairing to hold the final shape.

As used herein, a "staple" or "staple strand" is a nucleotide brick which pairs with a longer main body or scaffold brick in nucleotide origami to help fold the main body brick into the desired shape.

As used herein, a "nanobreadboard," "breadboard," or "template" is a total or final structure of a DNA structure or shape. For example, a mobile or immobile 4-arm junction, DNA origami happy face, rectangular brick, or double stranded DNA (dsDNA) in its final structure.

As used herein, an "architecture" is a one-, two-, or three-dimensional structure built using one or more bricks.

As used herein, "self-assembly" refers to the ability of nucleotides to anneal to each other, in a sequence-specific manner, in a predicted manner and without external control.

As used herein, a "toehold domain" is a short sequence of nucleotides that will bind fleetingly in the absence of additional binding, but greatly accelerates the initiation of strand displacement reactions. The toehold domain is typically between 4 and 10 nucleotides in length.

As used herein, a "specificity domain" ensures specific interaction between nucleotide oligomers and sufficiently long to ensure thermal stability.

As used herein, "sufficiently close" and "nanospaced" refers to a distance between two chromophores that allows one chromophore, when excited, to emit an exciton and transfer the exciton to a second chromophore without a loss of energy and near-field interactions occur.

A "ligand" is a type of binding protein that is recognized by a receptor and either causes the receptor to signal, an "agonist," or prevents the receptor to signal, an "antagonist."

As used herein the term "targeting molecule," "targeting peptide," "targeting moiety," or "targeting ligand" refers to any molecule that provides an enhanced affinity for a selected target, e.g., a cell, cell type, tissue, organ, region of the body, organic or inorganic compounds, oligomers, or a compartment, e.g., a cellular, tissue or organ compartment. The targeting molecule, peptide, moiety, or ligand can comprise a wide variety of entities. Such ligands can include naturally occurring molecules, or recombinant or synthetic molecules.

More specifically, a "targeting molecule" may be a protein or non-protein molecule which is characterized by selective binding to an organic or inorganic compound or oligomer.

More specifically, a "targeting peptide" is a peptide comprising a contiguous sequence of amino acids, which is characterized by selective localization to an organ, tissue, or cell type.

More specifically, a "targeting ligand" may be a protein or non-protein molecule which is characterized by selective localization to an organ, tissue, cell type, peptide, or antigen.

Exemplary targeting ligands include, but are not limited to, antibodies, antigen binding fragments of antibodies, antigens, folates, EGF, albumin, receptor ligands, carbohydrates, aptamers, integrin receptor ligands, chemokine receptor ligands, transferrin, biotin, serotonin receptor ligands, PSMA, endothelin, GCPII, somatostatin, LDL and HDL ligands. Additional exemplary ligands include, but are not limited to, polylysine (PLL), poly L-aspartic acid, poly L-glutamic acid, styrene-maleic acid anhydride copolymer, poly(L-lactide-co-glycolide) copolymer, divinyl ether-maleic anhydride copolymer, N-(2-hydroxypropyl)methacrylamide copolymer (HMPA), polyethylene glycol (e.g., PEG-2K, PEG-5K, PEG-10K, PEG-12K, PEG-15K, PEG-20K, PEG-40K), MPEG, [MPEG]2, polyvinyl alcohol (PVA), polyurethane, poly(2-ethylacrylic acid), N-isopropylacrylamide polymers, polyphosphazine, polyethylenimine, cationic groups, spermine, spermidine, polyamine, pseudopeptide-polyamine, peptidomimetic polyamine, dendrimer polyamine, arginine, amidine, protamine, cationic lipid, cationic porphyrin, quaternary salt of a polyamine, thyrotropin, melanotropin, lectin, glycoprotein, surfactant protein A, mucin, glycosylated polyaminoacids, transferrin, bisphosphonate, polyglutamate, polyaspartate, aptamer, asialofetuin, hyaluronan, procollagen, immunoglobulins (e.g., antibodies), insulin, transferrin, albumin, sugar-albumin conjugates, intercalating agents (e.g., acridines), cross-linkers (e.g. psoralen, mitomycin C), porphyrins (e.g., TPPC4, texaphyrin, Sapphyrin), polycyclic aromatic hydrocarbons (e.g., phenazine, dihydrophenazine), artificial endonucleases (e.g., EDTA), lipophilic molecules (e.g, steroids, bile acids, cholesterol, cholic acid, adamantane acetic acid, 1-pyrene butyric acid, dihydrotestosterone, 1,3-Bis-O(hexadecyl) glycerol, geranyloxyhexyl group, hexadecylglycerol, borneol, menthol, 1,3-propanediol, heptadecyl group, palmitic acid, myristic acid, O3-(oleoyl)lithocholic acid, O3-(oleoyl) cholenic acid, dimethoxytrityl, or phenoxazine), peptides (e.g., an alpha helical peptide, amphipathic peptide, RGD peptide, cell permeation peptide, endosomolytic/fusogenic peptide), alkylating agents, phosphate, amino, mercapto, polyamino, alkyl, substituted alkyl, radiolabeled markers, enzymes, haptens (e.g. biotin), transport/absorption facilitators (e.g., naproxen, aspirin, vitamin E, folic acid), synthetic ribonucleases (e.g., imidazole, bisimidazole, histamine, imidazole clusters, acridine-imidazole conjugates, Eu3+ complexes of tetraazamacrocycles), dinitrophenyl, HRP, AP, antibodies, hormones and hormone receptors, lectins, carbohydrates, multivalent carbohydrates, vitamins (e.g., vitamin A, vitamin E, vitamin K, vitamin B, e.g., folic acid, B12, riboflavin, biotin and pyridoxal), vitamin cofactors, lipopolysaccharide, an activator of p38 MAP kinase, an activator of NF-κB, taxon, vincristine, vinblastine, cytochalasin, nocodazole, japlakinolide, latrunculin A, phalloidin, swinholide A, indanocine, myoservin, tumor necrosis factor alpha (TNF□), interleukin-1 β, γ interferon, natural or recombinant low density lipoprotein (LDL), natural or recombinant high-density lipoprotein (HDL), and a cell-permeation agent (e.g., a. helical cell-permeation agent).

Peptide and peptidomimetic ligands include those having naturally occurring or modified peptides, e.g., D or L peptides; α, β, or γ peptides; N-methyl peptides; azapeptides; peptides having one or more amide, i.e., peptide, linkages replaced with one or more urea, thiourea, carbamate, or sulfonyl urea linkages; or cyclic peptides. A peptidomimetic (also referred to herein as an oligopeptidomimetic) is a molecule capable of folding into a defined three-dimensional structure similar to a natural peptide. The peptide or peptidomimetic ligand can be about 2-50 amino acids long, e.g., about 5, 10, 15, 20, 25, 30, 35, 40, 45, or 50 amino acids long.

Carbohydrate based targeting ligands include, but are not limited to, D-galactose, multivalent galactose, N-acetyl-D-galactose (GalNAc), multivalent GalNAc, e.g. GalNAc2 and GalNAc3; D-mannose, multivalent mannose, multivalent lactose, N-acetyl-galactosamine, N-acetyl-glucosamine, multivalent fucose, glycosylated polyaminoacids and lectins. The term multivalent indicates that more than one monosaccharide unit is present. Such monosaccharide sub-units can be linked to each other through glycosidic linkages or linked to a scaffold molecule.

"Binding" refers to a sequence-specific, non-covalent interaction between macromolecules (e.g., between a protein and a nucleic acid). Not all components of a binding interaction need be sequence-specific (e.g., contacts with phosphate residues in a DNA backbone), as long as the interaction as a whole is sequence-specific. Such interactions are generally characterized by a dissociation constant ($K_d$) of $10^{-6}$ $M^{-1}$ or lower. "Affinity" refers to the strength of binding: increased binding affinity being correlated with a lower Kd.

A "binding protein" is a protein that is able to bind non-covalently to another molecule. A binding protein can bind to, for example, a DNA molecule (a DNA-binding protein), an RNA molecule (an RNA-binding protein) and/or a protein molecule (a protein-binding protein). In the case of a protein-binding protein, it can bind to itself (to form homodimers, homotrimers, etc.) and/or it can bind to one or more molecules of a different protein or proteins. A binding protein can have more than one type of binding activity. For example, zinc finger proteins have DNA-binding, RNA-binding and protein-binding activity.

As used herein, the term "affinity peptide," "affinity moiety," or "affinity ligand" refers to any molecule that binds to a targeting ligand. Generally, the affinity ligand binds with the targeting ligand at a site that does not inhibit or reduce binding of the targeting ligand to its target.

Without limitations, the affinity ligand can be selected from the group consisting of small organic or inorganic molecules, peptides, proteins, peptide derivatives and analogs, peptidomimetics, nucleic acids, nucleic acid derivatives and acid analogs, saccharines, oligosaccharides, polysaccharides, lipids, glycoproteins, glycopeptides, and any combinations thereof.

The targeting peptide, targeting ligand, or affinity ligand can be linked to the molecule of interest via a linker. As used herein, the term "linker" means an organic moiety that connects two parts of a compound. Linkers typically comprise a direct bond or an atom such as oxygen or sulfur, a unit such as NH, C(O), C(O)NH, SO, $SO_2$, $SO_2$NH or a chain of atoms, such as substituted or unsubstituted alkyl, substituted or unsubstituted alkenyl, substituted or unsubstituted alkynyl, arylalkyl, arylalkenyl, arylalkynyl, heteroarylalkyl, heteroarylalkenyl, heteroarylalkynyl, heterocyclylalkyl, heterocyclylalkenyl, heterocyclylalkynyl, aryl, heteroaryl, heterocyclyl, cycloalkyl, cycloalkenyl, alkylarylalkyl, alkylarylalkenyl, alkylarylalkynyl, alkenylarylalkyl, alkenylarylalkenyl, alkenylarylalkynyl, alkynylarylalkyl, alkynylarylalkenyl, alkynylarylalkynyl, alkylheteroarylalkyl, alkylheteroarylalkenyl, alkylheteroarylalkynyl, alkenylheteroarylalkyl, alkenylheteroarylalkenyl, alkenylheteroarylalkynyl, alkynylheteroarylalkyl, alkynylheteroarylalkenyl, alkynylheteroarylalkynyl, alkylheterocyclylalkyl, alkylheterocyclylalkenyl, alkylhererocyclylalkynyl, alkenylheterocyclylalkyl, alkenylheterocyclylalkenyl, alkenylheterocyclylalkynyl, alkynylheterocyclylalkyl, alkynylheterocyclylalkenyl, alkynylheterocyclylalkynyl, alkylaryl, alkenylaryl, alkynylaryl, alkylheteroaryl, alkenylheteroaryl, alkynylhereroaryl, where one or more methylenes can be interrupted or terminated by O, S, S(O), $SO_2$, NH, C(O). The terms linker and spacer are used interchangeably herein. The linker can comprise any combinations of the above. Accordingly, in some embodiments, the linker can comprise hydrocarbons, amino acids, peptides, polyethylene glycol of various lengths, cyclodextrins, and derivatives and any combinations thereof.

A linker may also be a "branched linker." By a branched linker is meant a linker that can connect together three or more part together. The branch-point of the branched linker may be at least trivalent, but can be a tetravalent, pentavalent or hexavalent atom, or a group presenting such multiple valencies. In some embodiments, the branchpoint is —N, —N(Q)-C, —O—C, —S—C, —SS—C, —C(O)N(Q)-C, —OC(O)N(Q)-C, —N(Q)C(O)—C, or —N(Q)C(O)O—C; wherein Q is independently for each occurrence H or optionally substituted alkyl. In some embodiments, the branchpoint is glycerol or derivative thereof, and normal chain sugars such as monosaccharides and polysaccharides. A branched linker can be used to connect two or more (e.g., 2, 3, 4, 5, 6, 7, 8, 9, 10 or more) molecules of interest (which can be same or different) to one affinity ligand; two or more (e.g., 2, 3, 4, 5, 6, 7, 8, 9, 10 or more) affinity ligands (which can be same or different) to one molecule of interest; or two or more (e.g., 2, 3, 4, 5, 6, 7, 8, 9, 10 or more) molecules of interest (which can be same or different) to two or more (e.g., 2, 3, 4, 5, 6, 7, 8, 9, 10 or more) affinity ligands (which can be same or different).

A linker may comprise of at least one cleavable linking group. A cleavable linking group is one which is sufficiently stable outside the cell, but which upon entry into a target cell is cleaved to release the two parts the linker is holding together. In a preferred embodiment, the cleavable linking group is cleaved at least 10 times or more, preferably at least 100 times faster in the target cell or under a first reference condition (which can, e.g., be selected to mimic or represent intracellular conditions) than in the blood or serum of a subject, or under a second reference condition (which can, e.g., be selected to mimic or represent conditions found in the blood or serum).

Cleavable linking groups are susceptible to cleavage agents, e.g., pH, redox potential or the presence of degradative molecules. Generally, cleavage agents are more prevalent or found at higher levels or activities inside cells than in serum or blood. Examples of such degradative agents include: redox agents which are selected for particular substrates or which have no target specificity, including, e.g., oxidative or reductive enzymes or reductive agents such as mercaptans, present in cells, that can degrade a redox cleavable linking group by reduction; esterases; amidases; endosomes or agents that can create an acidic environment, e.g., those that result in a pH of five or lower; enzymes that can hydrolyze or degrade an acid cleavable linking group by acting as a general acid, peptidases (which can be target specific) and proteases, and phosphatases. The cleavable linking group can comprise esters, peptides, carbamates, acid-labile, reduction-labile, oxidation-labile, disulfides, and modifications thereof.

A linker can include a cleavable linking group that is cleavable by a particular enzyme. The type of cleavable linking group incorporated into a linker can depend on the cell to be targeted. In some embodiments, cleavable linking group is cleaved at least 1.25, 1.5, 1.75, 2, 3, 4, 5, 10, 25, 50, or 100 times faster in the cell (or under in vitro conditions selected to mimic intracellular conditions) as compared to blood or serum (or under in vitro conditions selected to mimic extracellular conditions). In some embodiments, the cleavable linking group is cleaved by less than 90%, 80%, 70%, 60%, 50%, 40%, 30%, 20%, 10%, 5%, or 1% in the blood (or in vitro conditions selected to mimic extracellular conditions) as compared to in the cell (or under in vitro conditions selected to mimic intracellular conditions).

Exemplary cleavable linking groups include, but are not limited to, redox cleavable linking groups (e.g., —S— and —C(R)2-S—, wherein R is H or C1-C6 alkyl and at least one R is C1-C6 alkyl such as CH3 or CH2CH3); phosphate-based cleavable linking groups (e.g., —O—P(O)(OR)—O—, —O—P(S)(OR)—O—, —O—P(S)(SR)—O—, —S—P(O)(OR)—O—, —O—P(O)(OR)—S—, —S—P(O)(OR)—S—, —O—P(S)(ORk)-S—, —S—P(S)(OR)—O—, —O—P(O)(R)—O—, —O—P(S)(R)—O—, —S—P(O)(R)—O—, —S—P(S)(R)—O—, —S—P(O)(R)—S—, —O—P(S)(R)—S—, —O—P(O)(OH)—O—, —O—P(S)(OH)—O—, —O—P(S)(SH)—O—, —S—P(O)(OH)—O—, —O—P(O)(OH)—S—, —S—P(O)(OH)—S—, —O—P(S)(OH)—S—, —S—P(S)(OH)—O—, —O—P(O)(H)—O—, —O—P(S)(H)—O—, —S—P(O)(H)—O—, —S—P(S)(H)—O—, —S—P(O)(H)—S—, and —O—P(S)(H)—S—, wherein R is optionally substituted linear or branched C1-C10 alkyl); acid cleavable linking groups (e.g., hydrazones, esters, and esters of amino acids, —C=NN— and —OC(O)—); ester-based cleavable linking groups (e.g., —C(O)O—); peptide-based cleavable linking groups, (e.g., linking groups that are cleaved by enzymes such as peptidases and proteases in cells, e.g., —NHCHRAC(O)NHCHRBC(O)—, where RA and RB are the R groups of the two adjacent amino acids). A peptide based cleavable linking group comprises two or more amino acids. In some embodiments, the peptide-based cleavage linkage comprises the amino acid sequence that is the target for a peptidase or a protease found in cells.

The cleavable linking group can be located anywhere in the linker. For example, the cleavable linking group can be located at a terminus of the linker. In some embodiments, the cleavable linking group is located at the linker terminus distal to the affinity ligand. In some embodiments, the cleavable linking group is located at the linker terminus distal to the molecule of interest, e.g., therapeutic agent. In some embodiments, the cleavable linking group is in the linker itself. In some embodiments, the cleavable linking group connects the linker to the molecule of interest, e.g., therapeutic agent. In some embodiments, the cleavable linking group connects the linker to the affinity ligand. Thus, in some embodiments of the invention, the linker can be linked to the affinity ligand and/or the molecule of interest via a cleavable linking group.

As used herein, a "sample" is a small part or quantity intended to represent the whole. For example, an environmental sample could be a small quantity of soil from a field or water from a lake. It could also be a blood or tissue sample. Sometimes the sample is purified to select an even smaller or more specific sample, such as isolating RNA or DNA from a blood or tissue sample.

Nucleotide Architecture

Nucleotide nanotechnology may be used to form simple or complicated one-, two-, and three-dimensional architectures. The nucleotide architectures may comprise of one or more nucleotide bricks. The nucleotide bricks are designed to use the Watson-Crick pairing of the nucleotides to cause the bricks to self-assemble into the final architectures. Any method of designing the architectures and self-assembly may be used such as, but not limited to, nucleotide origami, nucleotide brick molecular canvases, single stranded tile techniques, or any other method of nucleotide folding or nanoassembly such as, but not limited to, using nucleotide tiles, nucleotide scaffolds, nucleotide lattices, four-armed junction, double-crossover structures, nanotubes, static nucleotide structures, dynamically changeable nucleotide structures, or any other synthetic biology technique (as described in U.S. Pat. No. 9,073,962, U.S. Pub. No.: US 2017/0190573, U.S. Pub. No.: US 2015/0218204, U.S. Pub. No.: US 2018/0044372, or International Publication Number WO 2014/018675, each of which is incorporated by reference).

The nucleobase making up the bricks may be natural, including but not limited to, any of cytosine, uracil, adenine, guanine, thymine, hypoxanthine, or uric acid; or synthetic, including but not limited to methyl-substituted phenol analogs, hydrophobic base analogs, purine/pyrimidine mimics, icoC, isoG, thymidine analogs, fluorescent base analogs, or X or Y synthetic bases. Alternatively, a nucleotide may be abasic, such as but not limited to 3-hydroxy-2-hydroxymethyl-tetrahydrofuran, or alternatively a nucleotide analog may be used.

Non-limiting examples of synthetic nucleobases and analogs include, but are not limited to methyl-substituted phenyl analogs, such as but not limited to mono-, di-, tri-, or tatramethylated benzene analogs; hydrophobic base analogs, such as but not limited to 7-propynyl isocarbostyril nucleoside, isocarbostyril nucleoside, 3-methylnapthalene, azaindole, bromo phenyl derivates at positions 2, 3, and 4, cyano derivatives at positions 2, 3, and 4, and fluoro derivates at position 2 and 3; purine/pyrimidine mimics, such as but not limited to azole heterocyclic carboxamides, such as but not limited to (1H)-1,2,3-triazole-4-carboxamide, 1,2,4-triazole-3-carboxamide, 1,2,3-triazole-4-carboxamide, or 1,2-pyrazole-3-carboxamide, or heteroatom-containing purine mimics, such as furo or thieno pyridinones, such as but not limited to furo[2,3-c]pyridin-7(6H)-one, thieno[2,3-c]pyridin-7(6H)-one, furo[2,3-c]pyridin-7-thiol, furo[3,2-c]pyridin-4(5H)-one, thieno[3,2-c]pyridin-4(5H)-one, or furo[3,2-c]pyridin-4-thiol, or other mimics, such as but not limited to 5-phenyl-indolyl, 5-nitro-indolyl, 5-fluoro, 5-amino, 4-methylbenzimidazole, 6H,8H-3,4-dihydropropyrimido[4,5-c][1,2]oxazin-7-one, or $N^6$-methoxy-2,6-diaminopurine; isocytosine, isoquanosine; thymidine analogs, such as but not limited to 5-methylisocytosine, difluorotoluene, 3-toluene-1-β-D-deoxyriboside, 2,4-difluoro-5-toluene-1-β-D-deoxyriboside, 2,4-dichloro-5-toluene-1-β-D-deoxyriboside, 2,4-dibromo-5-toluene-1-β-D-deoxyriboside, 2,4-diiodo-5-toluene-1-β-D-deoxyriboside, 2-thiothymidine, 4-Se-thymidine; or fluorescent base analogs, such as but not limited to 2-aminopurine, 1,3-diaza-2-oxophenothiazine, 1,3-diaza-2- oxophenoxazine, pyrrolo-dC and derivatives, 3-MI, 6-MI, 6-MAP, or furan-modified bases.

Non-limiting examples of nucleotide analogs include, but are not limited to, phosorothioate nucleotides, 2'-O-methyl ribonucleotides, 2'-O-methoxy-ethyl ribonucleotides, peptide nucleotides, N3'-P5' phosphoroamidate, 2'-fluoro-arabino nucleotides, locked nucleotides (LNA), unlocked nucleotides (UNA), morpholino phosphoroamidate, cyclohexene nucleotides, tricyclo-deoxynucleotides, or triazole-linked nucleotides.

The nucleotides can then be polymerized into oligomers. The design of the oligomers will depend on the design of the overall architecture. Simple architectures may be designed by any methods. However, more complex architectures may be design using software, such as caDNAno (as described at cadnano.org/docs.html, and herein incorporated by reference), to minimize errors and time. The user may input the desired shape of the architecture into the software and once finalized, the software will provide the oligomer sequences of the bricks to create the desired architecture. The length of the oligomers may be from about 10 to about 10,000, or less than about 9,000, less than about 8,000, less than about 5,000 nucleotides in length. The length of the oligomer will be optimized for the type of architecture used.

In some embodiments the architecture is a single stranded hairpin loop with a toehold domain and a specificity domain, where the toehold domain and specificity domain will pair with a nucleotide oligomer of interest in a sample. The nucleotide oligomer of interest will initially bind to the toehold domain and then extend along the specificity domain, causing strand invasion of the stem of the hairpin. This causes the stem to open, separating the two strands of the stem as the oligomer of interest pairs with its complement strand. Hairpin loops may be from about 18 to about, from about 18 to about 50, from about 24 to about 50, from about 26 to about 50 nucleotides in length. A nucleotide oligomer may contain one or more hairpin loops.

In other embodiments the architecture is a single stranded hairpin loop bound to a targeting molecule. When the targeting molecule is bound by its corresponding target in a sample, the binding will cause the stem of the hairpin to open, separating the two strands of the stem.

In other embodiments the architecture is a single stranded loop where the loop of a single stranded hairpin loop is designed to be bound by a target, such as, but not limited to, a protein or small molecule which binds to nucleotide sequences, in a sample. The binding will cause the stem of the hairpin loop to open, separating the two strands of the stem. The target may either cleave the loop or cause a conformational change sufficient to separate the two strands of the stem.

In other embodiments the architecture is a double stranded nucleotide complex that may form a hairpin loop when the architecture detects a target in a sample. For example, a target nucleotide oligomer may bind to a toehold domain and expand along a specificity domain along one strand of the double stranded architecture. This may cause the opposite strand to leave the double stranded architecture. The opposite strand may then form a hairpin structure when free of the original double stranded architecture. A protein or other small molecule may also cause one strand to leave, allowing the opposite strand to form a hairpin structure. The strands of the double stranded nucleotide complex may be from about 10 to about 100, from about 10 to about 90, from about 10 to about 80, from about 10 to about 70, from about 10 to about 60, from about 10 to about 50, from about 10 to about 40, from about 10 to about 30, or from about 10 to about 20 nucleotides in length.

In other embodiments, two single stranded bricks are bound by a targeting molecule at complementary ends. When the ligands bind their targets in a sample, the bricks are brought together, forming a double stranded architecture.

In yet other embodiments, a single stranded nucleotide oligomer is brought together to form a hairpin loop by binding metal ions in a solution.

In other embodiments a double stranded architecture comprising of one longer nucleotide brick is pair to two shorter nucleotide bricks, where the two shorter bricks both have a toehold domain. One or both of the shorter bricks will then leave by strand invasion when bound by their target nucleotide oligomers.

In other embodiments, more complex single and double stranded architectures, such as four armed junctions (4AJ, FIG. 10A), for example Holliday Junctions, can be made using various toehold and specificity domains, for example see Zhang et al., *Engineering Entropy-Driven Reactions and Networks Catalyzed by DNA*, Science, 318: 1121-1125 (2007) and Cannon et al., *Large Davydov Splitting and Strong Fluorescence Suppression: An investigation of Exciton Delocalization in DNA-Templated Holliday Junction Dye Aggregates,* J. Phys. Chem. A, DOI: 10.1021/acs.jpca.7b12668, both herein incorporated by reference.

In some embodiments, the architecture is comprised of nucleotide brick molecular canvases, wherein the canvases are made of 1 to 5,000 nucleotide bricks comprising of nucleotide oligomers of 24 to 48 nucleotides and will self-assemble in a single reaction, a "single-pot" synthesis, as described in U.S. Pub. No.: US 2015/0218204. In more preferable embodiments, the canvases are made of 1 to 1,000 nucleotide bricks, from 1 to 750 nucleotide bricks, from 1 to 500 nucleotide bricks, or from 1 to 250 nucleotide bricks. In other embodiments, the oligomers comprise of 24 to 42 nucleotides, from 24 to 36 nucleotides, or from 26 to 36 nucleotides.

In another embodiment, the architecture is made step wise using a serial fluidic flow to build the final shape as described in U.S. Pat. No. 9,073,962.

In some embodiments, the architecture is assembled using the origami approach. With a DNA origami approach, for example, a long scaffold nucleic acid strand is folded to a predesigned shape through interactions with relatively shorter staple strands. Thus, in some embodiments, a single-stranded nucleic acid for assembly of a nucleic acid nanostructure has a length of at least 500 base pairs, at least 1 kilobase, at least 2 kilobases, at least 3 kilobases, at least 4 kilobases, at least 5 kilobases, at least 6 kilobases, at least 7 kilobases, at least 8 kilobases, at least 9 kilobases, or at least 10 kilobases. In some embodiments, a single-stranded nucleic acid for assembly of a nucleic acid nanostructure has a length of 500 base pairs to 10 kilobases, or more. In some embodiments, a single-stranded nucleic acid for assembly of a nucleic acid nanostructure has a length of 7 to 8 kilobases. In some embodiments, a single-stranded nucleic acid for assembly of a nucleic acid nanostructure comprises the M13 viral genome. In some embodiments the number of staple strands is less than about 500 staple strands, less than about 400 staple strands, less than about 300 staple strands, less than about 200 staple strands, or less than about 100 staple strands.

In some embodiments, the architecture is assembled from single-stranded tiles (SSTs) (see, e.g., Wei B. et al. Nature 485: 626, 2012, incorporated by reference herein) or nucleic acid "bricks" (see, e.g., Ke Y. et al. Science 388:1177, 2012;

International Publication Number WO 2014/018675 A1 each of which is incorporated by reference herein). For example, single-stranded 2- or 4-domain oligonucleotides self-assemble, through sequence-specific annealing, into two- and/or three-dimensional nanostructures in a predetermined (e.g., predicted) manner. As a result, the position of each oligonucleotide in the nanostructure is known. In this way, a nucleic acid nanostructure may be modified, for example, by adding, removing or replacing oligonucleotides at particular positions. The nanostructure may also be modified, for example, by attachment of moieties, at particular positions. This may be accomplished by using a modified oligonucleotide as a starting material or by modifying a particular oligonucleotide after the nanostructure is formed. Therefore, knowing the position of each of the starting oligonucleotides in the resultant nanostructure provides addressability to the nanostructure.

In some embodiments, the architecture is made from a single, single stranded oligomer, as described in U.S. Pub. No.: 2018/0044372. A single strand of DNA used for assembling a nanostructure in accordance with the present disclosure may vary in length. In some embodiments, a single strand of DNA has a length of 500 nucleotides to 10,000 nucleotides, or more. For example, a single strand of DNA may have a length of 500 to 9000 nucleotides, 500 to 8000 nucleotides, 500 to 7000 nucleotides, 500 to 6000 nucleotides, 500 to 5000 nucleotides, 500 to 4000 nucleotides, 500 to 3000 nucleotides, 500 to 2000 nucleotides, 500 to 1000 nucleotides, 1000 to 10000 nucleotides, 1000 to 9000 nucleotides, 1000 to 8000 nucleotides, 1000 to 7000 nucleotides, 1000 to 6000 nucleotides, 1000 to 5000 nucleotides, 1000 to 4000 nucleotides, 1000 to 3000 nucleotides, 1000 to 2000 nucleotides, 2000 to 10000 nucleotides, 2000 to 9000 nucleotides, 2000 to 8000 nucleotides, 2000 to 7000 nucleotides, 2000 to 6000 nucleotides, 2000 to 5000 nucleotides, 2000 to 4000 nucleotides, or 2000 to 3000 nucleotides. In some embodiments, a single strand of DNA may have a length of at least 2000 nucleotides, at least 3000 nucleotides, at least 4000 nucleotides, or at least 5000 nucleotides. In some embodiments, a single strand of DNA may have a length of 500, 600, 700, 800, 900, 1000, 1100, 1200, 1300, 1400, 1500, 1600, 1700, 1800, 1900, 2000, 2100, 2200, 2300, 2400, 2500, 2600, 2700, 2800, 2900, 3100, 3200, 3300, 3400, 3500, 3600, 3700, 3800, 3900, 4100, 4200, 4300, 4400, 4500, 4600, 4700, 4800, 4900, 5100, 5200, 5300, 5400, 5500, 5600, 5700, 5800, 5900, 6600, 6200, 6300, 6400, 6500, 6600, 6700, 6800, 6900, 7100, 7200, 7300, 7400, 7500, 7600, 7700, 7800, 7900, 8100, 8200, 8300, 8400, 8500, 8600, 8700, 8800, 8900, 9100, 9200, 9300, 9400, 9500, 9600, 9700, 9800, 9900, or 10000 nucleotides.

In some embodiments, the architecture is two-dimensional and comprises a single layer or bricks or a single scaffold. In other embodiments, the architecture is three-dimensional and may contain 2, 3, 4, 5, 6, 7, 8, 9, 10, 20, 30, or more layers of two-dimensional structures depending on the desired final shape.

In some embodiments, the architecture is attached to a substrate such as, but not limited to, a glass, silicone, plastic, or rubber base, paper, textile, nitrocellulose, calcium sulfate dihydrate, aggregates such as, but not limited to, concrete and cement, alumina- and/or silica-based building material, steel and other metals, plastics, acrylics, glass, wood, rubber, polyvinylidene difluoride membranes, or tissue such as, but not limited to, skin.

In other embodiments, the architecture remains in a solution. By altering aspects of the solution, such as but not limited to pH, sale concentrations, and cation charge, the aggregation of the bricks may be changed.

Chromophores

When chromophores aggregate in high concentrations in solution, exciton delocalization behavior (e.g. large Davydov splitting, exchange narrowing, quenching, superquenching, circular dichroism, Cotton effects, or Stokes shifting) from near-field interactions may be observed. When a chromophore is excited, an exciton is created, which is made of an electron and electron hole pair. This can also be thought of as an excited state and it is a quasi-particle. If two chromophores are sufficiently close to each other, the exciton may be transmitted or shared between neighboring without a loss in energy, hence, the exciton is delocalized. Chromophore based exciton delocalization effects and excitonic quantum coherent effects may occur at room temperature in wet and noisy environments and the systems may be less than about 100 nm. These systems provide several large benefits over the currently available quantum coherent systems, which are much larger, measuring in the micrometer size, and required extreme operating conditions, such as cryogenic temperatures, external magnetic fields and/or large microwave pulses, and dry environments, and usually involve a different quasi-particle. By binding the chromophores to a nucleotide architecture, various combinations can act as highly sensitive optical reporters.

Any chromophore in which an exciton can be created is acceptable may be used in any embodiment. A chromophore may be symmetrical or asymmetrical. By way of non-limiting examples, the chromophore may be one or more of a commercial chromophore(s), such as but not limited to Freedom™ Dye, Alexa Fluor® Dye, LI-COR IRDyes®, ATTO™ Dyes, Rhodamine Dyes, or WellRED Dyes; or any other dye. Examples of Freedom™ Dyes include 6-FAM, 6-FAM (Fluorescein), Fluorescein dT, Cy3™, TAMRA™, JOE, Cy5™, TAMRA, MAX, TET™, Cy5.5™, ROX, TYE™ 563, Yakima Yellow®, HEX, TEX 615, TYE™ 665, TYE 705, and Dyomic Dyes. Examples of Alexa Fluor® Dyes include Alexa Fluor® 488, 532, 546, 647, 660, and 750. Examples of LI-COR IRDyes® include 5' IRDye® 700, 800, and 800CW. Examples of ATTO™ Dyes include ATTO™ 488, 532, 550, 565, Rho101, 590, 633, 647N. Examples of Rhodamine Dyes include Rhodamine Green™-X, Rhodamine Red™-X, and 5-TAMRA™. Examples of WellREd Dyes include WellRED D4, D3, and D2. Examples of Dyomic Dyes include Dy-530, -547, -547P1, -548, -549, -549P1, -550, -554, -555, -556, -560, -590, -591, -594, -605, -610, -615, -630, -631, -632, -633, -634, -635, -636, -647, -647P1, -648, -648P1, -649, -649P1, -650, -651, -652, -654, -675, -676, -677, -678, -679P1, -680, -681, -682, -700, -701, -703, -704, -705, 730, -731, -732, -734, -749, -749P1, -750, -751, -752, 754, -756, -757, -758, -780, -781, -782, -800, -831, -480XL, -481XL, -485XL, -510XL, -511XL, -520XL, -521XL, -601XL. Examples of other dyes include 6-FAM, Fluorescein, Texas Red®-X, and Lightcycler® 640.

Using the above architectures, two or more chromophores may be precisely placed with nanometer precision apart from each other. When so placed, the chromophores may produce delocalized and/or quantum coherent excitons, biexcitons, and triexcitons when excited by a light source. In some exemplary embodiments, the two or more chromophores are covalently bound to the same nucleotides brick, and then the chromophore bound brick and non-bound bricks, if any, may self-assemble into the desired final one-, two-, or three-dimensional shape. In another embodiment, the chromophores are bound to separate nucleotide bricks or oligomers and come sufficiently close to form near-field interactions when the final architecture forms.

In yet another embodiment, the bricks are allowed to first self-assemble into the desired final one-, two-, or three-dimensional shape. Portions of the bricks may still be unpaired after assembly, allowing for further binding of complementary oligomers. The two or more chromophores are bound to at least one complementary oligomer which may then pair with the one or more unpaired portions of the bricks.

Figure 1B:
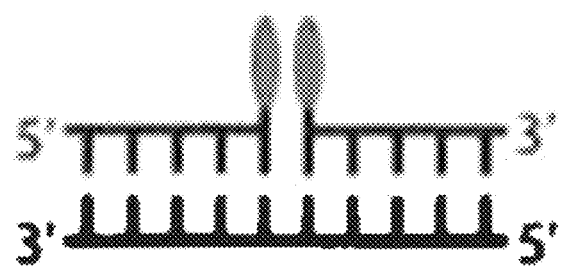
FIG. 1B is a schematic representation of a simple nucleotide brick bringing together two chromophore bound separate bricks, one with a chromophore bound to the 3' end and the other to the 5' end.
Figure 1C:
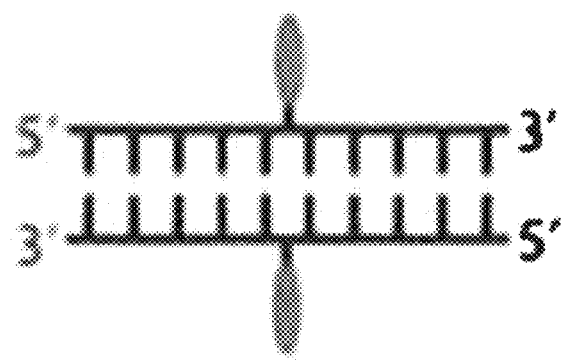
FIG. 1C is a schematic representation of two simple nucleotide bricks, either bound with a chromophore, with the chromophore bound internally in both bricks.
Figure 1D:
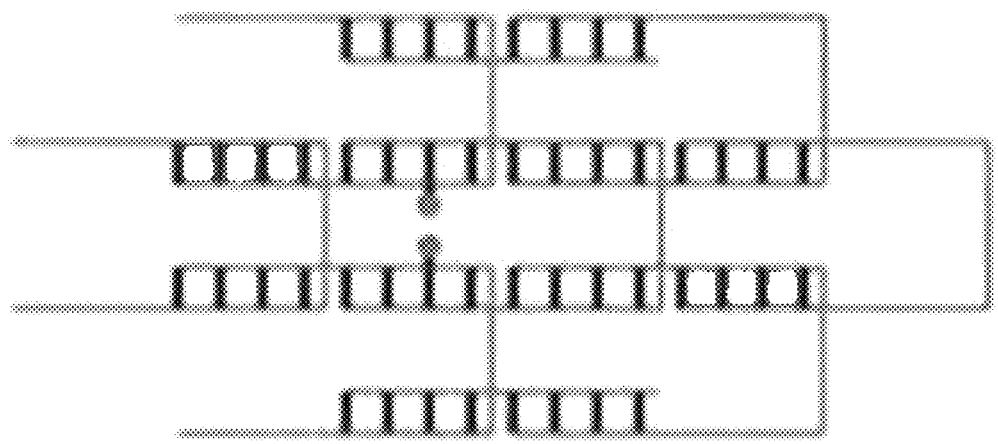
FIG. 1D is a schematic representation of a canvas with two of the bricks bound with a chromophore internally and on different nucleotide duplexes.

In some embodiments, the chromophores are bound to the 5' ends of the nucleotide bricks or oligomers (FIG. 1A). In other embodiments, the chromophores are bound to the 3' ends of the nucleotide bricks. In yet other embodiments, the chromophores are bound internally within the nucleotide bricks (FIGS. 1C and 1D). In still more embodiments, the chromophores are bound to any mix of 5' ends, 3' ends, or internally (FIG. 1B). The position of the chromophore will depend on the desired final configuration. Methods of binding chromophores to nucleotides is well known in the art.

In some embodiments, the chromophores are bound to the same nucleotide duplex (FIGS. 1A-1C). In other embodiments, the chromophores are bound to separate nucleotide duplexes (FIG. 1D).

The orientation of the two or more chromophore dipoles to each other effect the absorbance and emission spectra. Depending on the orientation, a pair of chromophores sufficiently close to form near-field interactions, nanospaced apart, will have different characteristics when compared to the monomer chromophore. When the dipoles are parallel, an "H-dimer" forms, which are characterized by a blue-shift in absorbance due to having a higher excited energy state when compared to the monomer. When the dipoles are in a head-to-head orientation, a "J-dimer" forms, which is characterized by a red-shirt in absorbance due to having a lower excited energy state when compared to the monomer. When the dipoles are at an oblique angle, a mixed "J/H-dimer" forms and is characterized by Davydov splitting due to having both a higher and lower excited energy state when compared to a monomer (see FIG. 2).

Figure 3A:
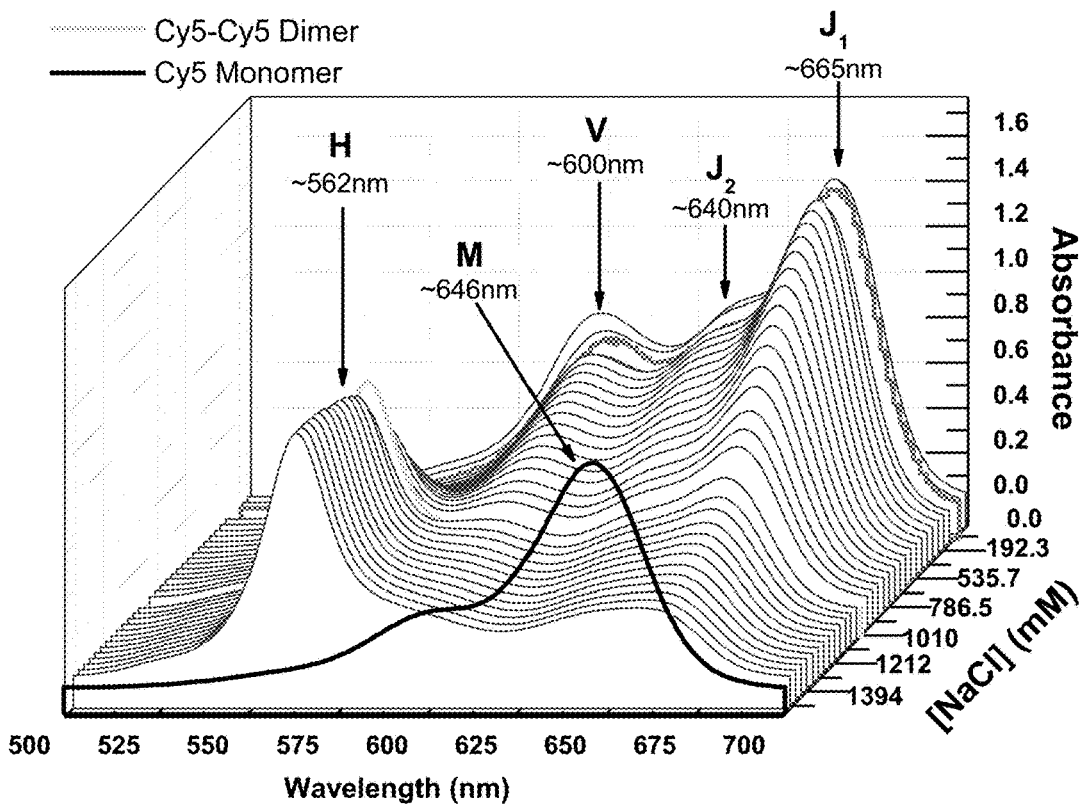
FIG. 3A is a graphical representation of changes in absorbance.
Figure 3B:
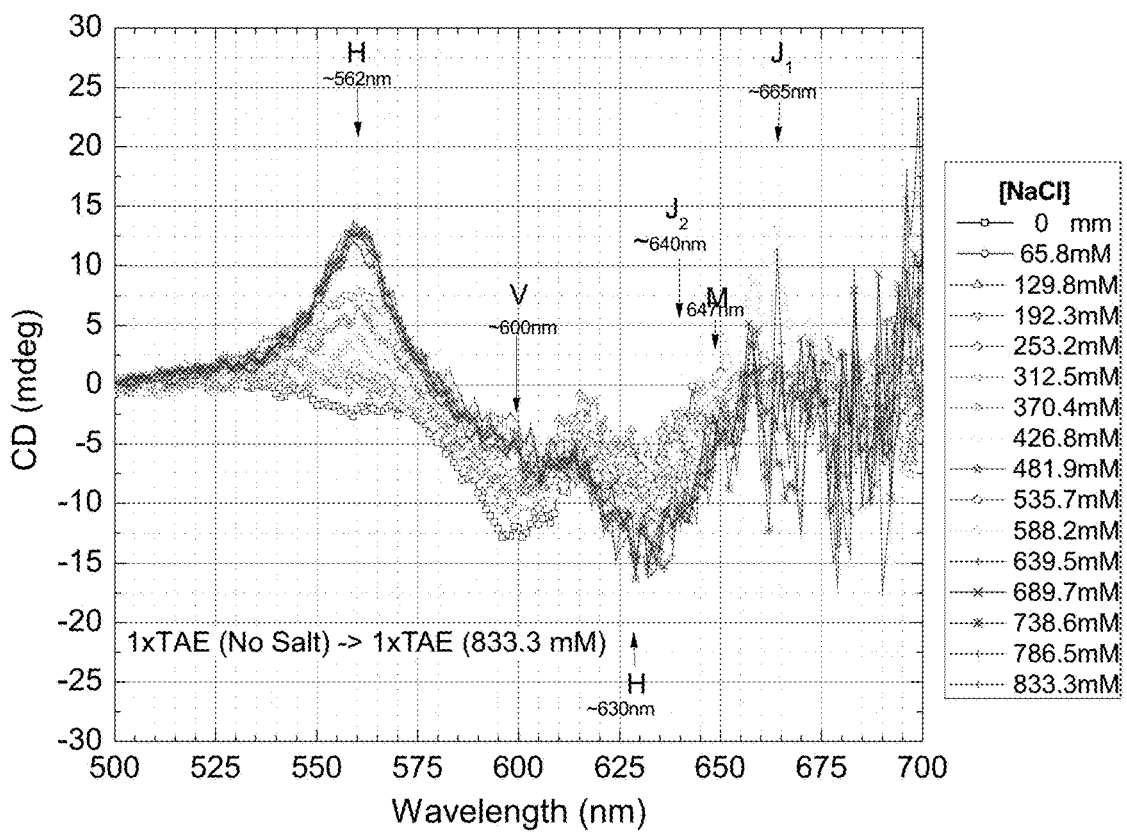
FIG. 3B is a graphical representation of circular dichroism.
Figure 3C:
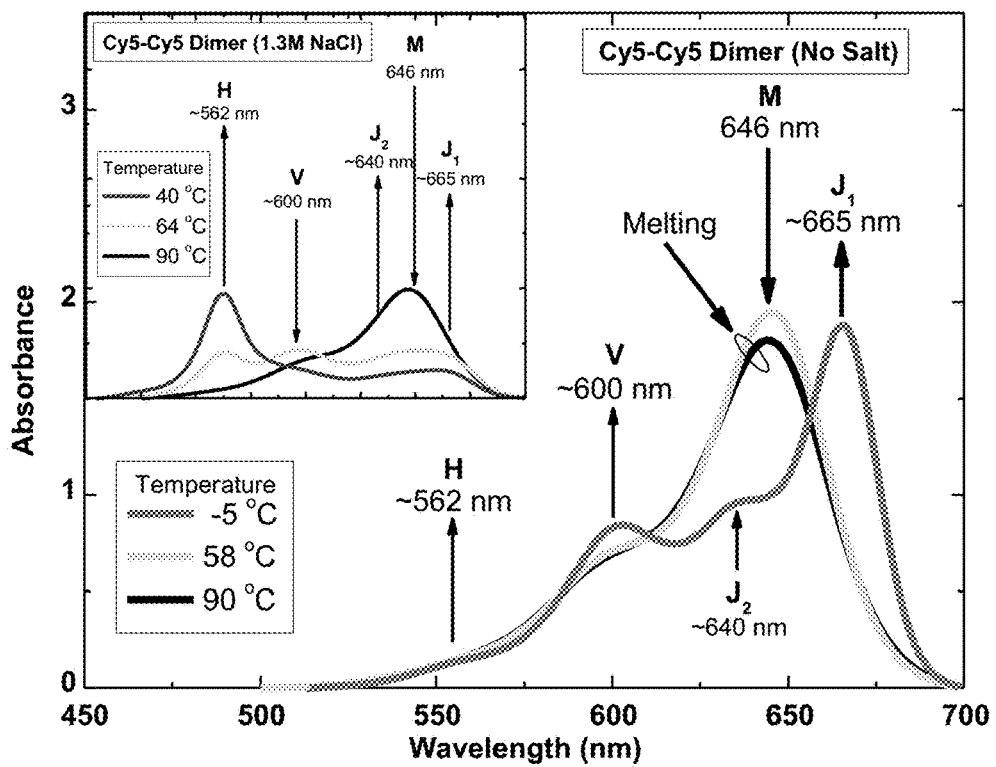
FIG. 3C is a graphical representation of changes to salt concentration, absorbance with changes in temperature.
Figure 3D:
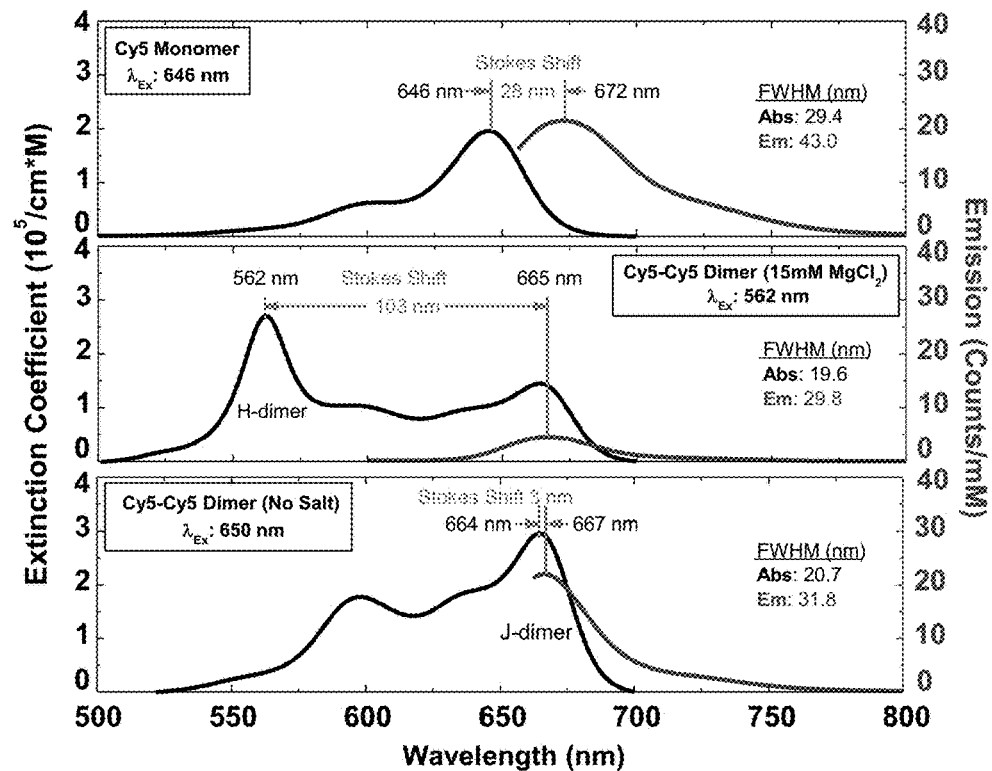
FIG. 3D is a graphical representation of emission with changes to salt concentration.

The orientation of two or more chromophores on a linear oligomer, which affects the absorbance spectra, is also affected by characteristics of the solution, including salt concentration (FIG. 3A), temperature (FIG. 3C), and cation concentration. Therefore, by altering the conditions of the solution, it is possible to fine tune the absorbance spectra of the chromophores nanospaced from each other. As shown in FIGS. 3A and 3B, as the salt concentration increases, a chromophore dimer may be fine-tuned to exhibit either J-dimer characteristics at lower salt concentrations or H-dimer characteristics at high salt concentrations. FIG. 3C further shows that by altering both the temperature and salt concentrations, it is further possible to tune the chromophores for specific characteristics. FIG. 3D shows that not only the absorbance, but the emission is altered by changing the concentration of salt in the solution.

Figure 4A:
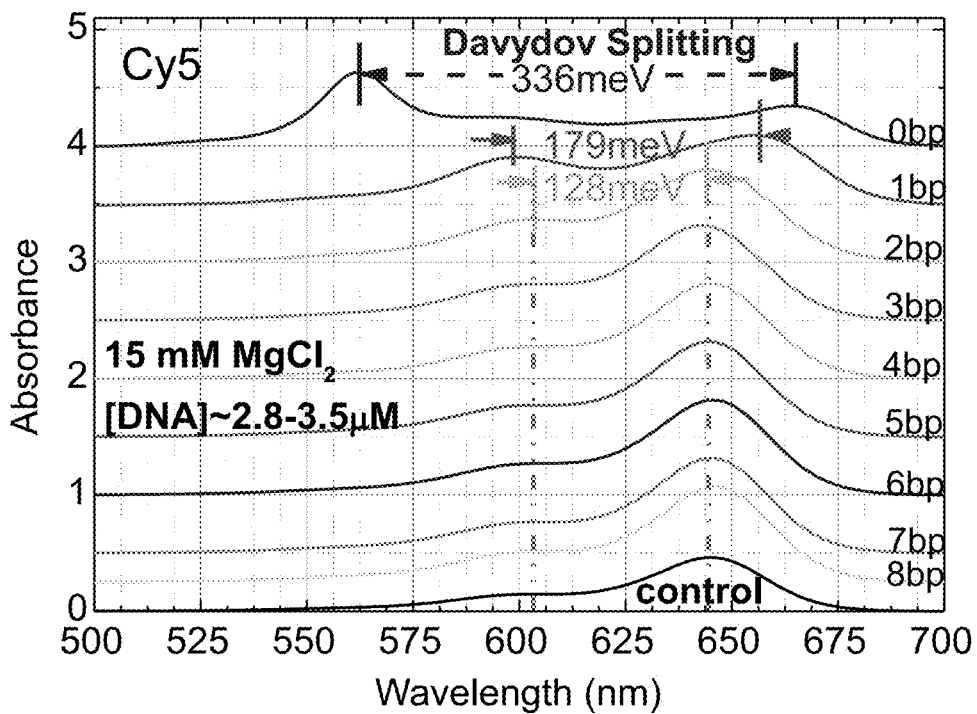
FIG. 4A is a graphical representation of the changes in absorbance versus wavelength as a function of Cy5 dimer separation examined by varying the number of nucleotides between monomers.
Figure 4B:
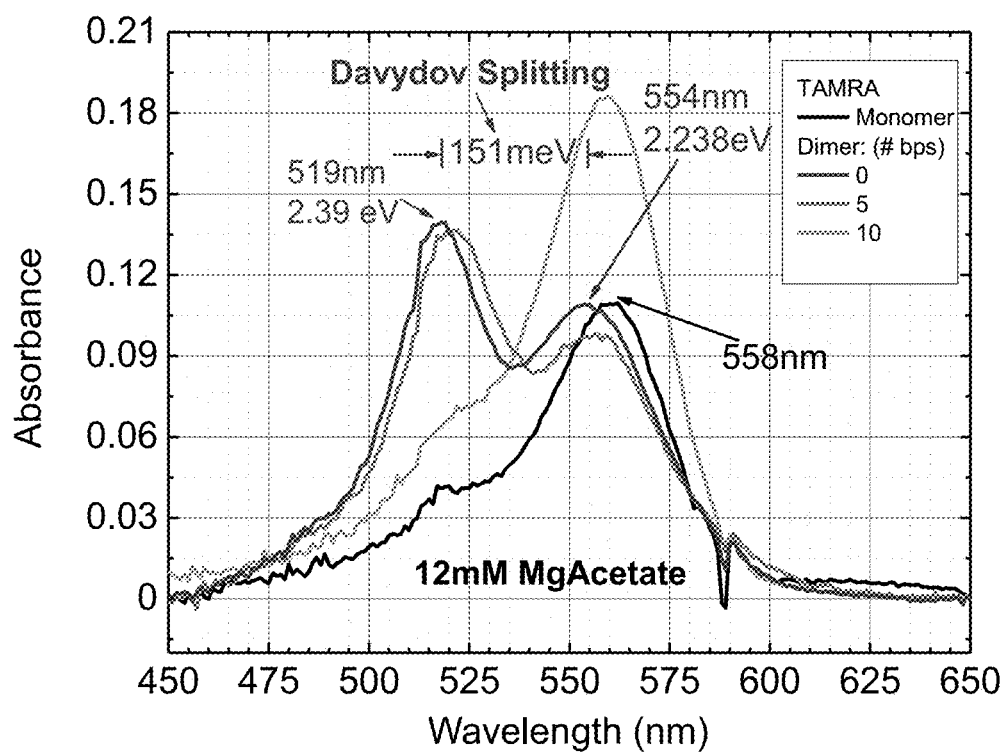
FIG. 4B is a graphical representation of the changes in absorbance versus wavelength as a function of TAMRA dimer separation examined by varying the number of nucleotides between monomers.

Additionally, the absorbance spectrum of the two chromophores on a linear oligomer is also affected by the nanospacing of two chromophores. As the distance increases, the Davydov splitting disappears and the absorbance spectrum approaches that of a monomer (FIGS. 4A and 4B). As shown in FIGS. 4A and 4B, as two chromophores are moved apart, the Davydov splitting seen when the chromophores are sufficiently close from each other disappears. Further, as shown by FIGS. 4A and 4B the distance in which the Davydov splitting is lost is different for different chromophores.

Taken together, by altering the composition of the solution surrounding the nucleotide architecture and by altering the distance between the chromophores, one skilled in the art may alter the absorbance and emission spectra for two or more chromophores bound to a nucleotide architecture to fine tune toward dimer type.

Figure 5:
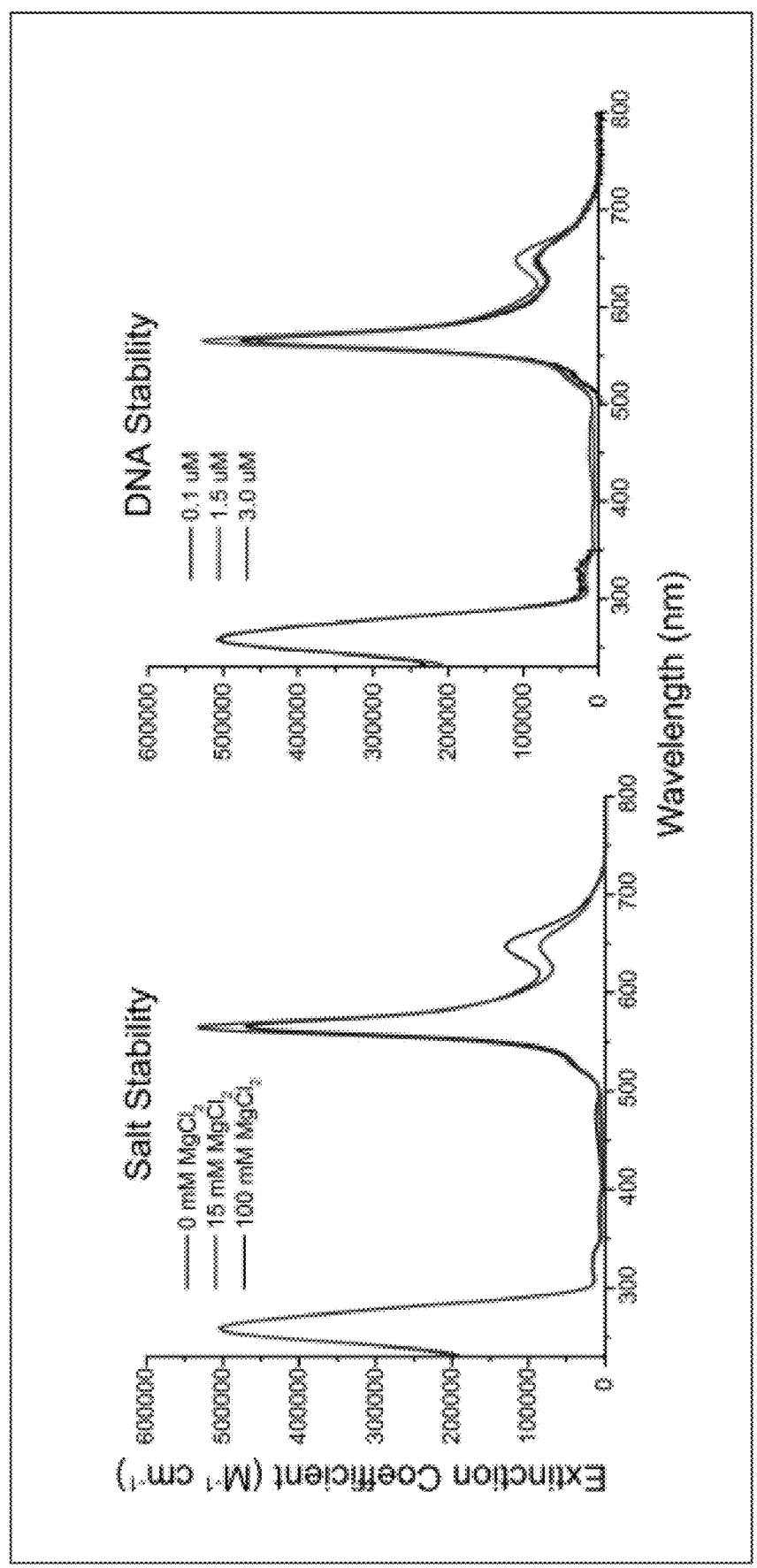
FIG. 5 is a graphical representation of the stability of a chromophore tetramer attached to an immobile 4-arm junction template in varying amounts of salt or DNA concentration.

When more rigid nucleotide structures are used, such as but not limited to Holiday Junctions (a type of immobile 4-arm junction), the architecture is more capable of holding the chromophores in a rigid position, losing the flexibility seen in the linear strands (FIG. 5).

In various embodiments, the nucleotide architecture holds the chromophores in precise nanospaced positions to control the near-filed interactions to obtain desired changes in the absorbance and emittance spectrums by controlling which dimers form.

In an embodiment two chromophores are held by an architecture nanospaced head to tail to form a J-dimer. In another embodiment, two chromophores are held by an architecture in parallel nanospaced to form a H-dimer. In another embodiment, two chromophores are held oblique to each other by an architecture to form a mixed J/H-dimer.

In another embodiment, three chromophores are positioned within the architecture so that two of the three chromophores form a J-dimer, and two of the three chromophores form a H-dimer. In a different embodiment, the chromophores are positioned such that two form a J-dimer and the third forms two mixed J/H-dimers. In yet another embodiment, two of the chromophores form a H-dimer and the third forms two mixed J/H-dimers.

In yet another embodiment, a tetramer of chromophores is positioned within the architecture such that two H-dimers, two J-dimers, and two mixed J/H-dimers are formed. In other embodiments, the tetramer can be position so that two H-dimers and four mixed J/H-dimers are formed. In yet another embodiment, the tetramer is positioned so that two J-dimers and four mixed J/H-dimers are formed.

In other embodiments, the dimer, trimers, and tetramers as described above can be joined with other monomers, dimer, trimers, and tetramers in order to form more complex multimers to alter the absorbance and emittance spectrum.

Due to the changes in absorbance and emission seen when two or more chromophores are sufficiently close when attached to various nucleotide architectures, such as hairpin loops or double stranded complexes with toehold domains, these compositions are useful as highly sensitive optical reporters, such as chromic detectors, as ink, as chromic photoswitches, and/or molecular rulers.

Chromic Detection

Most colorimetric detection schemes are based on light emission or light scattering of single particles which does not alter the energy band structure. However, the near-field interaction between sufficiently close chromophores changes the energy band structure which results in a change of the absorption spectrum that produces a color change. The color change may be detected by the eye, sometimes even unaided, in ambient light much more easily than fluorescence changes. This color change may be particularly useful for applications where the eye rather than expensive and/or large footprint instrumentation, is used as the detector. Such applications may include point of service medical diagnostic application particularly in a home or outside a clinical setting. In addition, using aptamers, this detection mechanism can be extended to detect chemical constituents other than nucleic acids. The use of this invention as an aptamer readout greatly broadens the range of potential applications in medical diagnostics, agriculture, veterinary, and biological sciences. In addition, aptamers allow this detection scheme to be extended to detect nonbiological chemical constituents.

Using single stranded nucleotide architectures, such as hairpin loops or individual single strands, or double stranded nucleotide architectures and chromophores placed sufficiently close to each other on the architectures, with the optional addition of targeting molecules, a variety of compounds may be detected in a sample.

Figure 7:
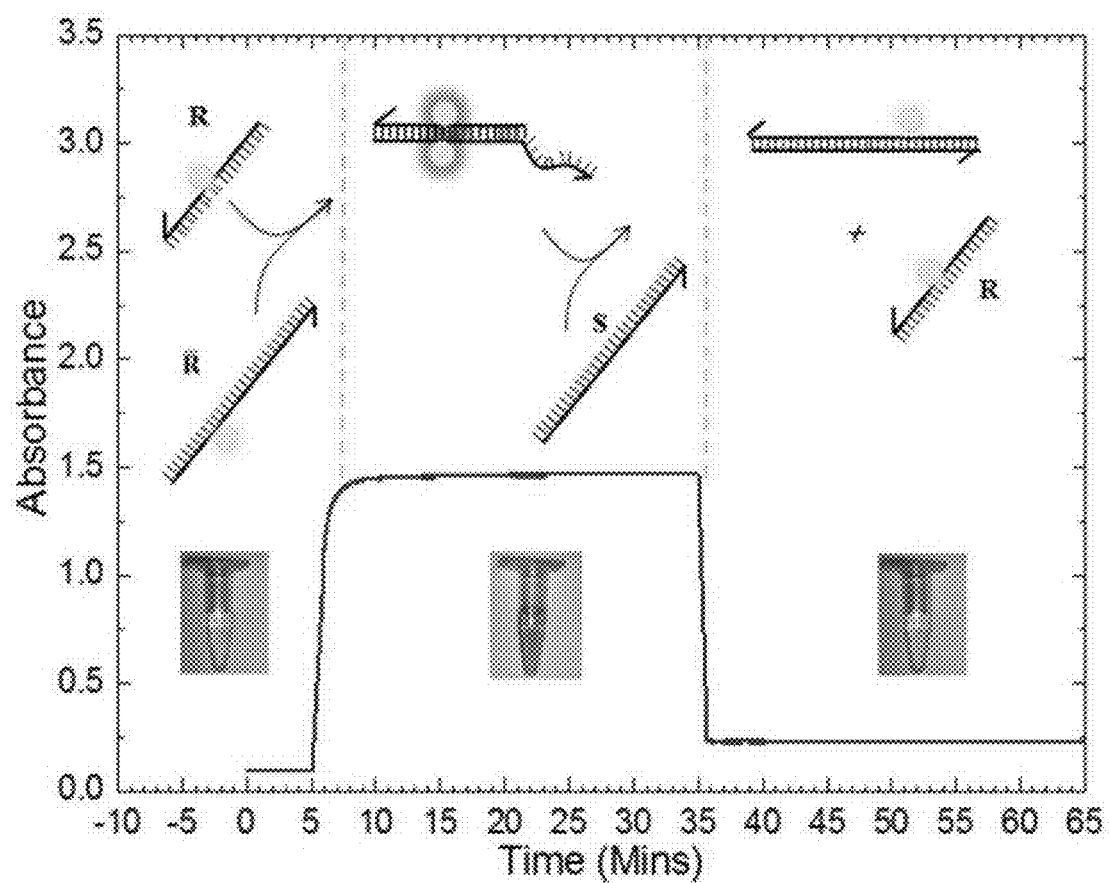
FIG. 7 is a graphical representation of absorption at 563 nm verses time showing activating and deactivating a functional dimer and the associated color change due to Davydov splitting with respect to the schematic of the DNA reaction network.

By way of non-limiting examples, a double stranded nucleotide complex which when paired brings two chromophores which are sufficiently close so that the chromophores form near-filed interactions which result in a change in absorption when compared to the monomers (see FIG. 7). This results in the solution changing color upon the formation of the dimer. One of the two strands comprising the architecture contains a toehold domain that will complement a target sequence that may be within the sample. As shown in FIG. 7, once the target sequence first binds the toehold domain, it will displace the complement strand by strand invasion with the other chromophore attached. This will result in the formation of monomers within the sample, undoing the near-field interactions, and causing the solution to change color.

Figure 8A:
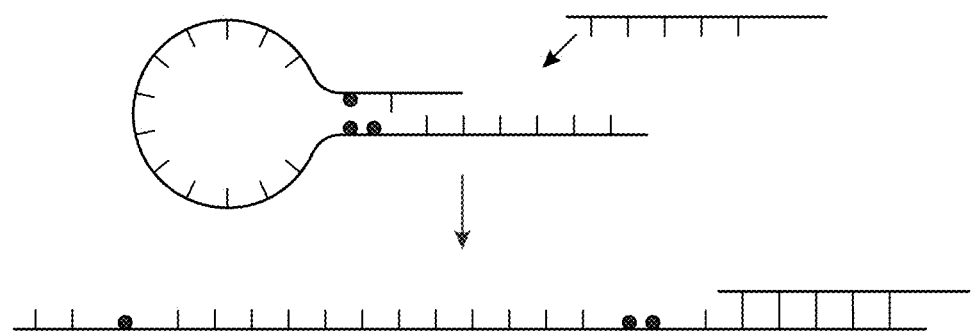
FIG. 8A is a schematic representation of a single strand RNA hairpin with three chromophores that will form a monomer and a dimer upon strand separation such as by strand invasion by a target oligomer which may be used in either detection assays or in an ink.
Figure 8B:
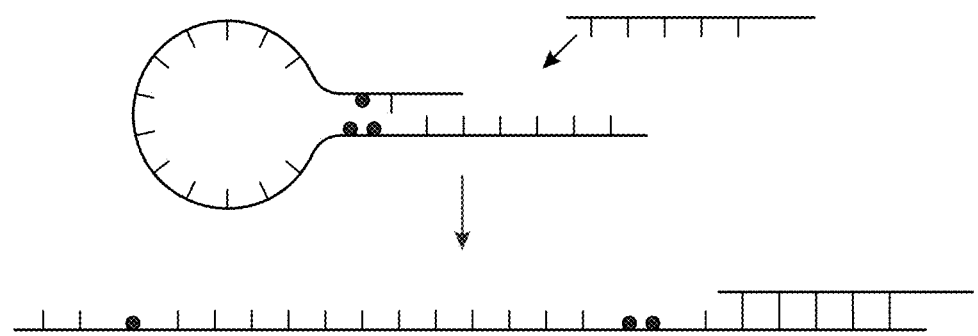
FIG. 8B is a schematic representation of a single strand RNA hairpin with three chromophores that will form three monomers upon strand separation such as by strand invasion by a target oligomer which may be used in either detection assays or in an ink.

Additional structures and placement of chromophores may also be used for the detection of various compounds in a solution. FIGS. 8A-8B show schematic representations of non-limiting examples using hairpin loops bound to trimers of chromophores. While the hairpin loop is closed, the resulting trimer produces one color in solution or sample due to the near-field interactions. However, upon invasion of the target strand in the solution, the hairpin loop opens, displacing separating the trimer into either a monomer and a dimer or three monomers, resulting in a change in color of the solution or sample.

Figure 8C:
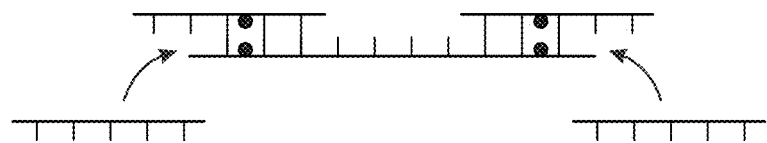
FIG. 8C is a schematic representation of a linear double stranded nucleotide comprised of three nucleotide bricks which may be used in either direction assays or in an ink. One brick provides a scaffold and the two other bricks comprise a toehold domain. When the three bricks are assembled, two chromophore dimers with near-filed interference form that will disassociate into four monomers when both toehold bricks bind their respective targets.

Double stranded architectures may also contain more than two oligomers. By way of non-limiting example, as depicted in FIG. 8C, a single longer brick, such as a scaffold brick, may be bound to two other bricks, where the two other bricks contain toehold domains. Each of the two other bricks may detect the same target or two different targets. When the toehold bricks are bound to scaffold brick, two dimers are formed which absorb light differently than each would as a monomer. The chromophores may be the same or different, so a variety of different colors may be produced. Through strand invasion, one or both bricks containing the toehold domains may be displaced, which may result in a variety of color changes.

In another non-limiting example, two single or double stranded architectures with toehold domains at one end and a chromophore bound at a distal end, will only bring the chromophores in close enough proximity when both toehold domains are bound by a target within a sample. In another non-limiting example, the multiple architectures have toehold domains on each side, which may target one or two targets before the chromophores are brought sufficiently close to cause near-field interactions and to change the color of the solution or sample.

In other non-limiting examples, the toehold domains may be replaced with targeting molecules. These targeting molecules may bind to a variety of compounds within a sample to cause displacement or joining of chromophores.

More complex architectures, such as 4AJ (see for example FIG. 10), nucleotide origami, or canvases, may also be used. The more complex architectures may allow for the same architecture to be used for the detection of multiple targets using different chromophores to cause a variety of color changes. For example, a two-dimensional canvas architecture may comprise of bricks which are paired to single stranded oligomers with toehold domains or targeting molecules and when paired, two chromophores are brought sufficiently close for near-field interactions to result. Each of the toehold domains or targeting molecules may have a different target to detect across broad ranges of compounds at once. Depending on the chromophores used, both the intensity of light and/or a color change may be detected to determine the output of the detection.

Ink

One may write with a nucleotide ink of one color and then they may change that color by adding the complement. Additionally, any printing technology that may disperse an aqueous solution may be used to create inexpensive colorimetric arrays for assaying various compounds.

By way of a non-limiting example, an ink may comprise of single or double stranded nucleotide architecture bound to one or more chromophores. If the architecture is single stranded, it may be a linear or hairpin structure. If the architecture is double stranded, it may be linear or branched, such as a 4AJ. The ink may further comprise of an acceptable vehicle which may comprise pH modifiers, humectants to retard premature drying, polymeric resins to impart binding and allied properties, defoamer/antifoaming agents to regulate foam efficiency, wetting agents such as surfactant to control surface properties, biocides to inhibit the fungal and bacterial growth that lead to fouling, thickeners or rheology modifiers to control ink application, other inorganic materials such as clay to serve as fillers or extenders, and water. The final makeup of the vehicle will depend on how the ink is used and may be tailored for specific uses.

The ink may be laid down on any acceptable surface such as, but not limited to, paper or other wood pulp products, textiles, calcium sulfate dihydrate, aggregates such as, but not limited to, concrete and cement, alumina- and/or silica-based building material, steel and other metals, plastics, acrylics, glass, wood, rubber, nitrocellulose, polyvinylidene difluoride membranes, or tissue such as, but not limited to, skin. The vehicle will aid in drying and adhering the chromophore bound nucleotide architecture to an acceptable surface.

The ink may be laid down by any means, such as using a pen or printer. For example, a cartridge may be filled with the ink composition, the cartridge may then be loaded into a pen, and the pen used to write on paper. The cartridge may instead fit inside of an ink jet printer, and the printer may lay down he in on paper.

Inks may also be mixed. By way of non-limiting example, a first ink may be laid down onto an acceptable surface and then a second ink may be laid down over the first ink. The two inks may contain complementary nucleotide architectures, such as linear complement strands, which may then pair and bring chromophores sufficiently close to cause near-field interference which will result in a visible color change of the ink. For example, multiple pens each housing a different ink may be used sequentially, or a printer loaded with multiple inks in multiple cartridges may lay the inks down to obtain the desired colors. Optionally, one ink may be an invasive strand which may cause a double stranded or a single stranded hairpin look to disassociate and cause chromophores sufficiently close to cause near-field interference to separate, losing the near-field interference and result in a color change. More complex inks may also be used, such as a pair of inks that may act as a chromic photoswitch.

In an embodiment, an ink jet printer may be loaded with multiple inks, where the inks comprise of nucleotide architecture and chromophores to create printable assays, for example nucleotide oligomer, protein, or environmental assays. The ink may be printed onto an acceptable surface in any pattern. Different ink may be printed to discrete spots onto the acceptable surface. The architecture in the ink may contain toehold domains for strand invasion or targeting molecules for other molecules, such as volatile organic compounds or proteins. Upon either strand invasion or target binding, the location the ink is printed on will undergo a color change due to a change architecture disrupting the chromophore placement.

Chromic Photoswitch

Excitonic switches such as through described in Hannestad et al., *Self-Assembled DNA-Based Fluorescence Waveguide with Selectable Output*, Small, 7: 3178-3185 (2011), Stein et al., *Single-Molecule Four-Color FRET Visualizes Energy-Transfer Paths on DNA Origami*, J. Am. Chem. Society, 133: 4193-4195 (2011), and Graugnard et al., *DNA-Controlled Excitonic Switches*, 12: 2117-2122 (2012) (all herein incorporated by reference).

Figure 9:
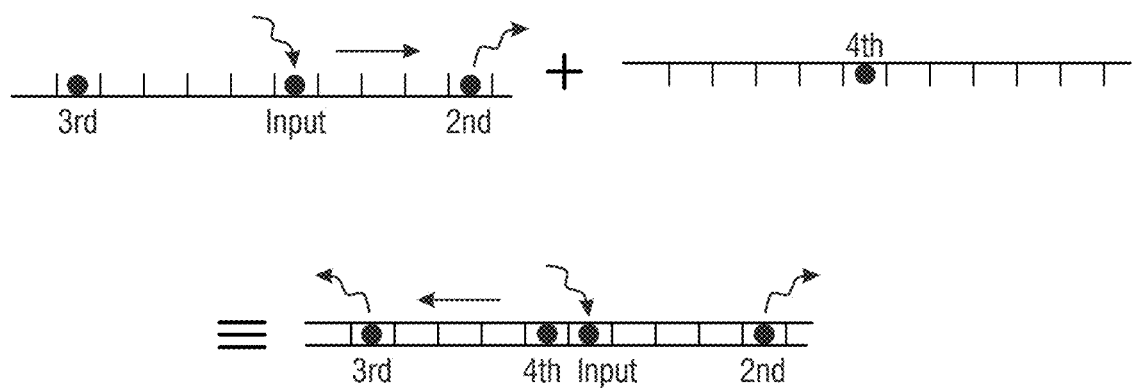
FIG. 9 is a schematic representation of a variation of an exemplary chromic photoswitch. A first single stranded nucleotide stranding comprising the input chromophore and two other chromophores is bound to a second single stranded nucleotide comprising a fourth chromophore. The binding of the nucleotide strands brings the fourth chromophore sufficient close to alter the absorbance spectra of the input chromophore.

As a non-limiting example and as depicted in FIG. 9, a chromic photo switch may comprise of a linear double stranded nucleotide architecture. The first strand may contain three different chromophores. A central chromophore acting as an input chromophore and two other chromophores acting as output chromophores. The two output chromophores are not sufficiently close to create near-field interference with the input chromophore but may still undergo FRET. Therefore, the output chromophores may be about 2 nm to about 10 nm apart. The first output chromophore has an overlapping absorbance with the emittance of the input chromophore and will fluoresce. The second output chromophore cannot absorb the light emitted by the input chromophore and will therefore not fluoresce. To cause the "switch," a second strand is bound to the first strand. The second strand comprises a fourth chromophore. When the first and second strand bind, the fourth chromophore is brought sufficiently close to the input chromophore, causing near-field interference, and thus altering the absorbance and emittance spectrum. The second output chromophore is selected to be capable of absorbing the emitted light from the input/fourth chromophore dimer and will thus fluoresce while the first output chromophore may no longer be capable of absorbing the light emitted by the dimer.

In another non-limiting example, the fourth chromophore may cause quenching or superquenching of the emittance of the input chromophore, so there is not output, or reduced output, from the chromic photoswitch. This example of a chromic photoswitch may or may not have output chromophores.

In one embodiment, the photoswitches may be incorporated in bioinspired synthetic photosynthetic systems as photoprotective agents and/or for self-repair capabilities that are currently only found in nature. In another embodiment, they may also be incorporated into dye sensitized photovoltaics or solar cells in which two chromophores incorporated rather than one dye if the incoming light is better suited for chromophore than the other chromophore. In a further embodiment, the active dye can be changed via nucleotide strand invasion.

Chromic Molecular Ruler

Most molecular rulers are based on a near-field coupling, FRET. FRET near-field coupling does not change the energy band structure of each chromophore. The near-field coupling experienced between the two chromophores in the embodiments changes the energy band structure in which the two chromophores act as one chromophore. The result is that the absorption and emission behavior and the exciton interaction energy of the two chromophores change. For this effect to occur, the two chromophores may be about 2 nm apart or closer. For FRET-based molecular rulers, the chromophores are usually between about 3 to about 5 nm apart. Hence, the chromic molecular rulers work at closer distances and are more sensitive that the FRET based molecular rulers.

By way of non-limiting example, nucleotide architecture bound to chromophores may be designed to bind a target, either through toehold domains or targeting molecules. If the architecture is single stranded, both the 5' and 3' end of the architecture may bind to a separate target. If the targets are sufficiently close, they may bring the chromophores to within sufficiently close distance for near-field interference to cause a change in the absorbance of the newly formed dimer. In the opposite, if the two binding sites are too distant, a change in absorbance will not be measured.

The invention is further described in detail by reference to the following experimental examples. These examples are provided for purposes of illustration only and are not intended to be limiting unless otherwise specified. Thus, the invention should in no way be construed as being limited to the following examples, but rather, should be construed to encompass any and all variations which become evident as a result of the teaching provided herein.

EXAMPLES

Example 1

Figure 2A:
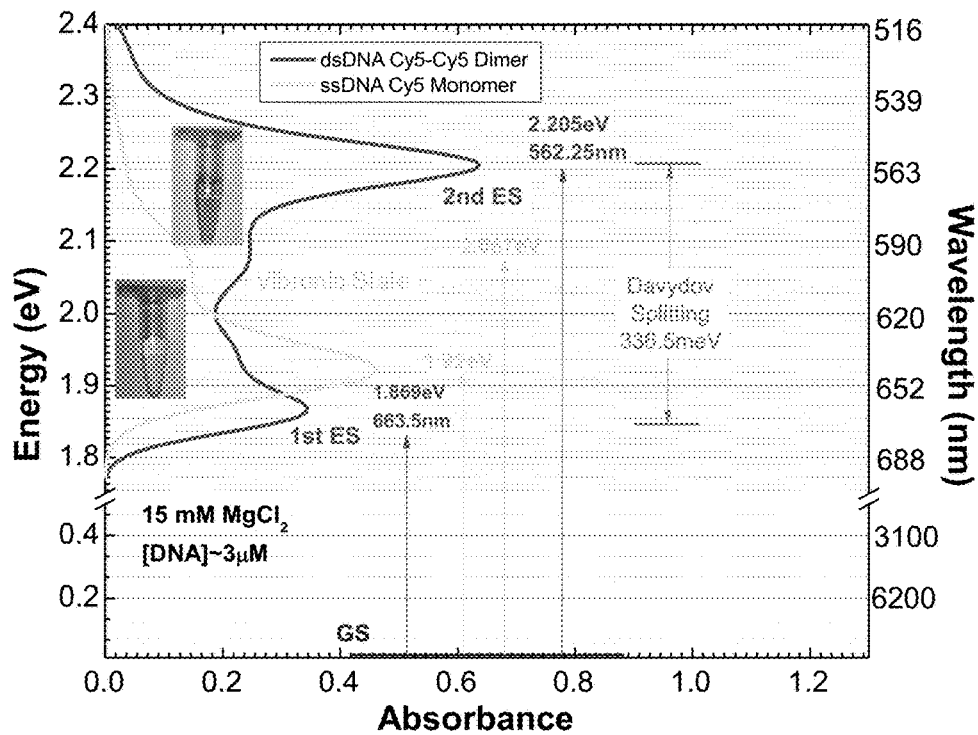
FIG. 2A is a graphical representation of the absorbance versus energy of (i) Cy5 chromophore covalently attached to a single stranded DNA (ssDNA-Cy5) monomer with one primary exciton absorption peak; (ii) a Cy5-Cy5 dimer on double stranded DNA (dsDNA-Cy5 dimer) showing Davydov splitting causing two exciton absorption peaks: 1st excited state (ES) at 1.87 eV from ground state (GS) shows J-Dimer characteristics due to the red shift from the monomer; 2nd ES at 2.205 eV shows H-Dimer characteristics due to the shift from the monomer. Davydov splitting shows the Cy5 pairs are at oblique angles. Taken in typical room light conditions, the micrographs show the Davydov splitting of Cy5-Dy5 dimer causes visible color change to the unaided eye due to the splitting being more than about 150 nm. The micrograph also shows observations consistent with exchange narrowing.

To determine the position of a Cy5-Cy5 dimer bound to a nucleic acid oligomer, the absorbance and energy were measured over a range of wavelengths, covering the known absorbance and emittance wavelengths of Cy5, ranging from about 500 nm to about 6200 nm and compared to a Cy5 monomer (see FIG. 2A).

The absorbance verses energy of a Cy5 monomer attached to a linear single stranded DNA oligomer (ssDNA-Cy5) was compared to Cy5-Cy5 dimer attached to a double stranded DNA oligomer (dsDNA-Cy5) in the presence of 15 mM $MgCl_2$. The concentration of DNA was about 3 µM. The monomer and dimer were exposed to increasing wavelengths of light and the absorbance and energy was measured.

As shown in FIG. 2A, the monomer has one primary absorption peat at 1.92 eV. In comparison, the dimer showed Davydov splitting, having two exciton absorption peaks, one at 1.87 eV and one at 2.205 eV. The 1.87 eV peak, a red shift from the monomer peak, shows the presence of J-dimer behavior. The 2.205 eV peak, a blue shift from the monomer peak, shows the presence of H-dimer behavior. As shown in the micrograph, this split causes a visible color change to the unaided eye. FIG. 2A also shows the presence of exchange narrowing, as the two peaks of the dimer show a narrower excitation range than the monomer.

Figure 2B:
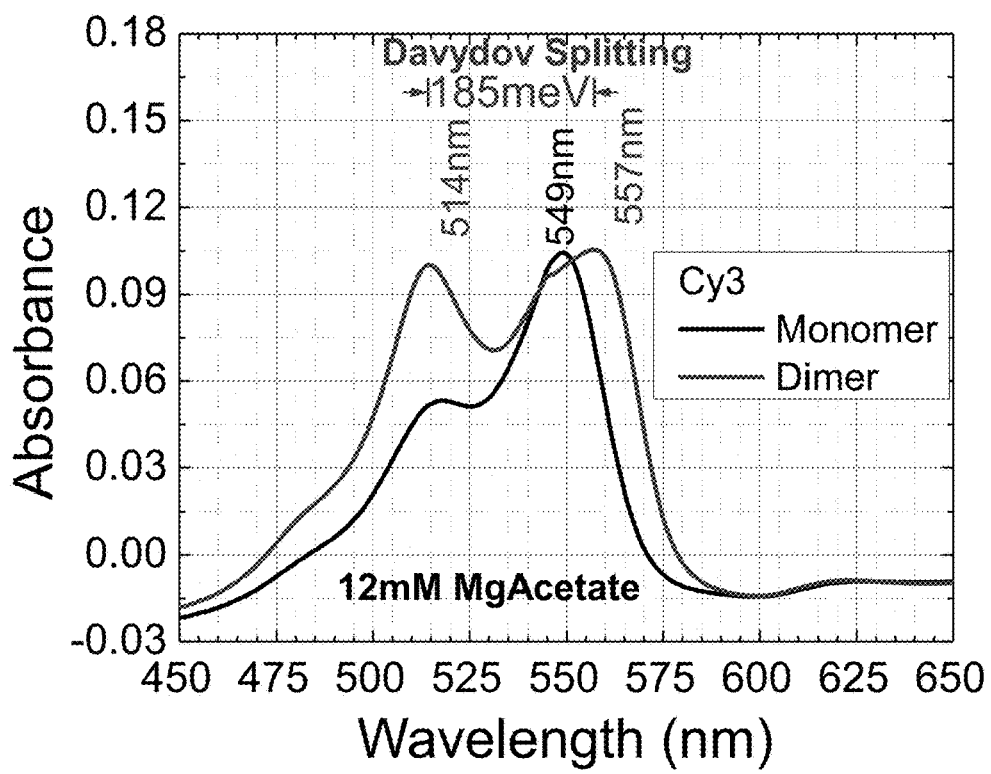
FIG. 2B is a graphical representation of the Cy3 dimer absorbance at different wavelengths compared to the Cy3 monomer.

Cy3 dimers were also compared to Cy3 monomers (FIG. 2B). Both the dimer and the monomer were exposed to about 450 nm to about 650 nm light and the absorbance was measured. The Cy3 dimer, like the Cy5 dimer, showed a Davydov shift, having characteristics of both J-dimers and H-dimers.

Due to the presence of the Davydov splitting, showing both a red and blue shift when compared to the monomer, the orientation of the chromophores on the dsDNA-Cy5 can be determined to be at an oblique angle to each other. The oblique position of chromophores allows for the two different energy states because the other dimers, J-dimers and H-dimers do not permit the two excited energy states.

Example 2

To measure the flexibility of the dsDNA-Cy5 on a linear strand of nucleic acid, the conditions of the solution and temperature were altered to detect changes in the absorbance spectrum.

The linear dsDNA-Cy5 strands were exposed to wavelengths of about 500 to about 700 nm. The salt concentrations were altered from 0 to about 1500 mM of NaCl. As shown in FIG. 3A, as the concentration of salt increased, dsDNA-Cy5 showed a reduction in Davydov splitting ($J_1$-V peaks), and a loss of J-dimer characteristics ($J_1$ peak). At about 1000 mM NaCl, dsDNA-Cy5 showed a loss of J-dimer characteristics, with a result of just H-dimer characteristics when compared to the ssDNA-Cy5 monomer. As shown in FIG. 3B, an increase in salt levels from 0 to about 909 mM NaCl showed the CD changed as well, with 0 mM salt showing Davydov splitting and J-dimer characteristics and 909 nM NaCl showing H-dimer characteristics. The change in CD shows that polarization and angle of the chromophore may also be optimized. This is important for stimulating specific chromophores, such as input chromophores, for quantum computing.

Changing both the salt concentrations and temperature also showed a change in absorbance verses wavelength of the dsDNA-Cy5 in a solution of 1×TAE buffer (FIG. 3C). The dsDNA-Cy5 composition was also compared to the ssDNA-Cy5 composition. When comparing no salt with 4.8 µM DNA compared to 1.3 M NaCl with 4.3 µM DNA a strong J-dimer peak appears without an H-dimer in the no salt whereas the 1.3 M NaCl shows a strong H-dimer peak without a J-dimer peak. Exchange narrowing, compared to the monomer peak, is evident for both the J-dimer and the H-dimer. Temperature changes also showed an effect as it got closer to the melting temperature for the double stranded DNA. As the temperature increased, both the J-dimer (with no salt) and the H-dimer (with 1.3 M NaCl) resulted in absorbance spectra more similar to the monomer.

The Stokes Shift was also affected by a change in salt concentration. As shown in FIG. 3D, at 15 mM $MgCl_2$ the Stokes Shift increased from 28 nm, the Stokes Shift of the Cy5 monomer, increases to 103 nm due to the red shift of the H-dimer lowers the Extinction Coefficient. At no salt, in the presence of the J-dimer, the Stokes Shift narrowed to 3 nm.

Due to the flexibility of the dsDNA-Cy5, it is possible for one skilled in the art to use salt and temperature to fine tune the orientation on a linear oligomer.

Example 3

To determine the effect of separation on the absorbance spectrum, the number of nucleotides to which the chromophores were bound along a linear oligomer were varied for different dyes.

As shown in in FIG. 4A, two Cy5 chromophores were bound from 0 to 8 nucleotides apart on a double stranded DNA oligomer and keeping the salt concentration of the solution at 15 mM $MgCl_2$. As shown, as the distance increased the absorbance spectrum of the Cy5 chromophores exhibited dimer characteristics, as evidenced by the Davydov splitting, at close distances of about 2 nucleotides (bp) or less. At 3 nucleotides and more the Cy5 chromophores exhibited monomer characteristics. In contrast, TAMRA chromophores in a 12 mM MgAcetate solution showed dimer characteristics when spaced further apart from each other, maintaining dimer characteristics at least until 5 nucleotides apart (FIG. 4B). The dimerization characteristics for TAMRA was lost at 10 nucleotides as measured by the change in absorbance spectrum.

Therefore, to maintain dimer characteristics, the individual chromophore molecules must remain near each other or they will act like monomers.

Example 4

To measure the effect of using more complicated and rigid architectures on chromophore behavior, the chromophores were bonded to an immobile four arm-junction architecture (4AJ, i.e. Holliday junction) (see Cannon et al., *Large Davydov Splitting and Strong Fluorescence Suppression: An Investigation of Exciton Delocalization in DNA-Templated Holliday Junction Dye Aggregates*, 2018, J. Phys. Chem. A, doi:10.1021/acs.jpca.7b12668, Supplemental Information, herein incorporated by reference), while the salt and DNA concentration in the solution were varied.

As shown in FIG. 5, as the salt concentration increases from 0 to 15 to 100 mM $MgCl_2$, there is no change in the extinction coefficient over wavelengths ranging from 0 to about 800 nm. Similarly, as the DNA concentration increased from 0.1 to 1.5 to 3.0 µM, there was also no change in the extinction coefficient over the same range of wavelengths.

Therefore, in contrast to a linear strand of DNA which may be tuned using salt concentrations, a more rigid architecture can more securely fix a chromophore in place, stabilizing the chromophores. This would allow one skilled in the art to select either a rigid or flexible system, or a combination thereof, to better form quantum wires and circuits of the desired shapes and absorbance spectra.

Example 5

Figure 6A:
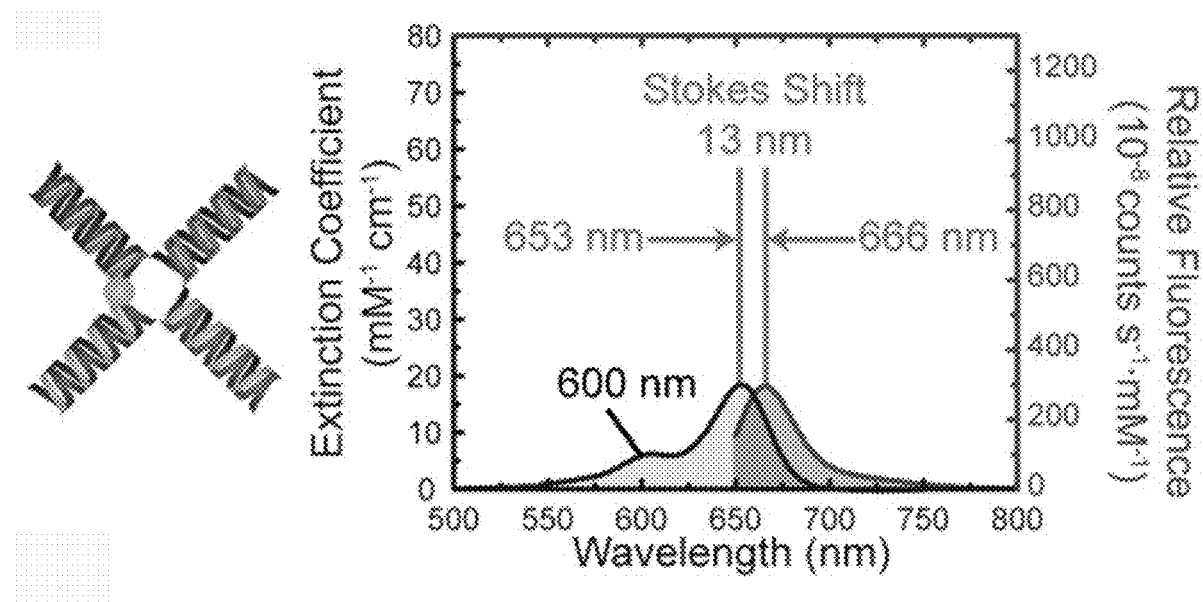
FIG. 6A is a graphical representation of the fluorescence spectra of a 4-arm junction (4AJ) templated Cy5 monomer.
Figure 6B:
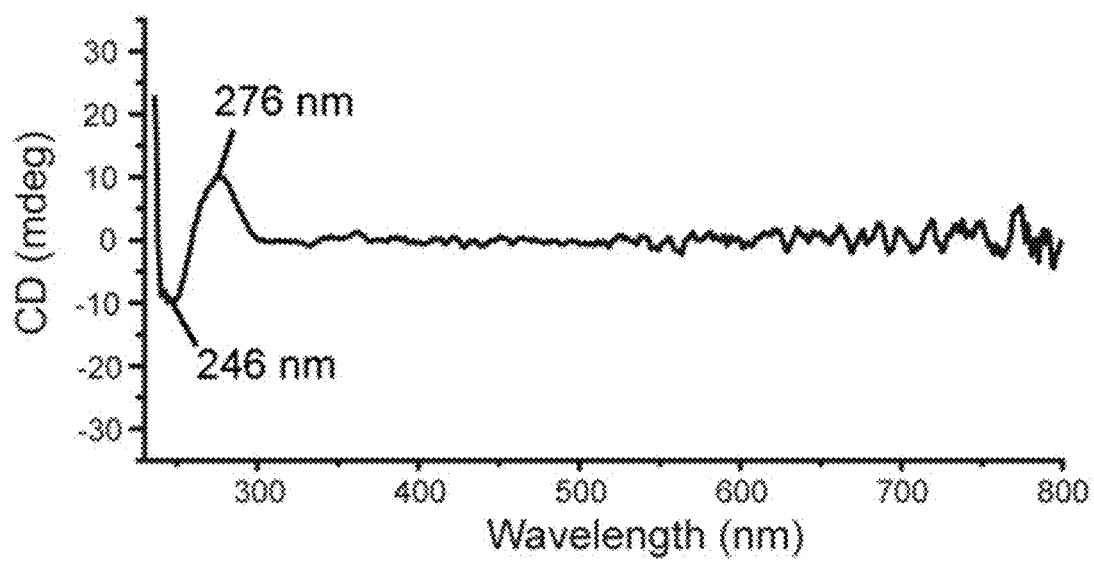
FIG. 6B is the CD of a 4AJ templated Cy5 monomer.
Figure 6C:
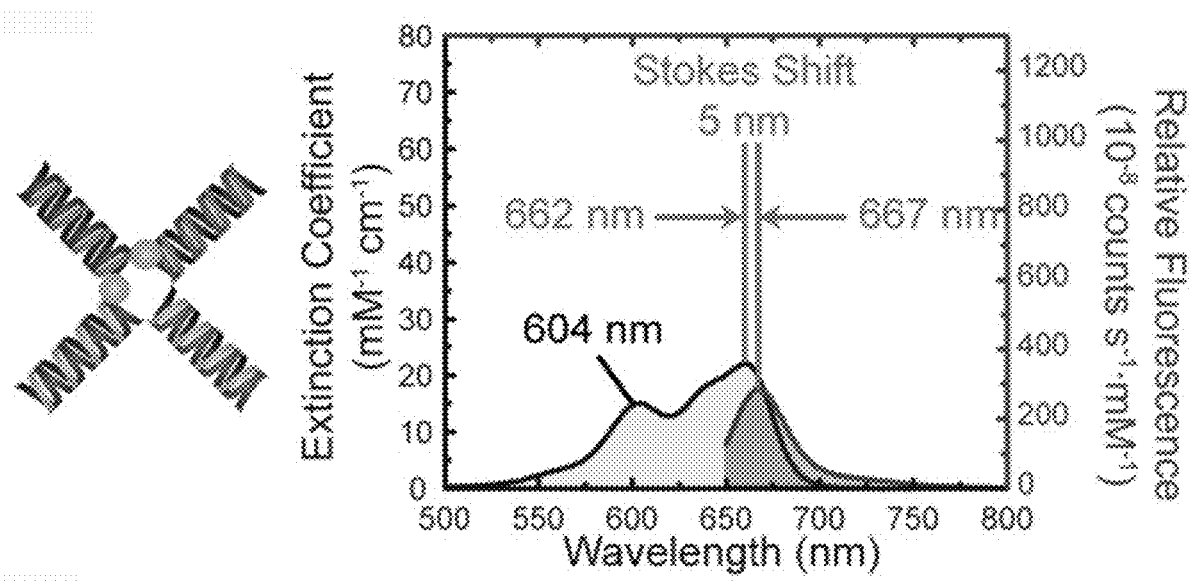
FIG. 6C is the fluorescence spectra of a 4AJ templated Cy5 adjacent dimer.
Figure 6D:
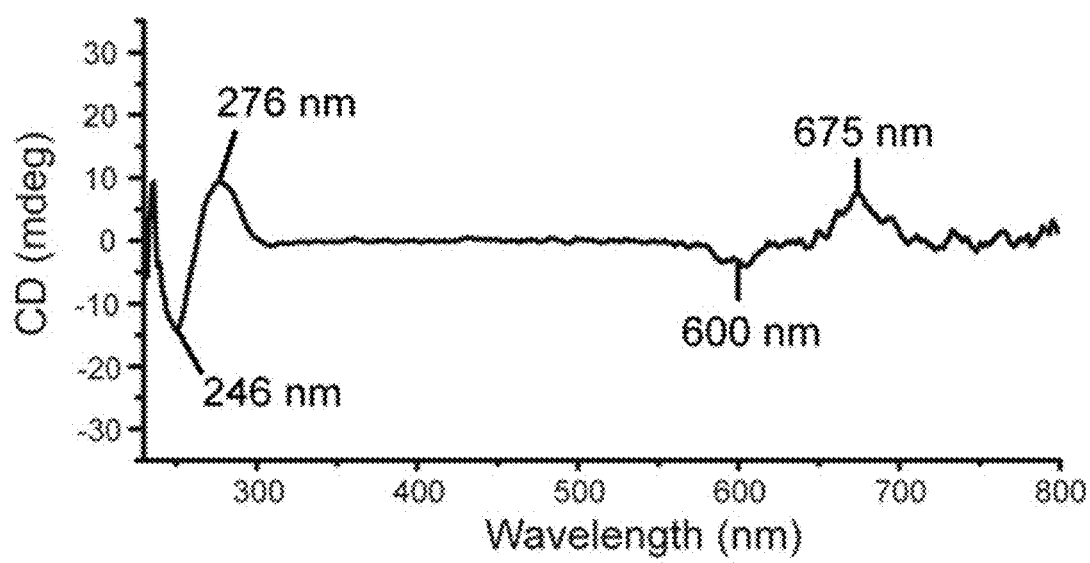
FIG. 6D is the CD of a 4AJ templated Cy5 adjacent dimer.
Figure 6E:
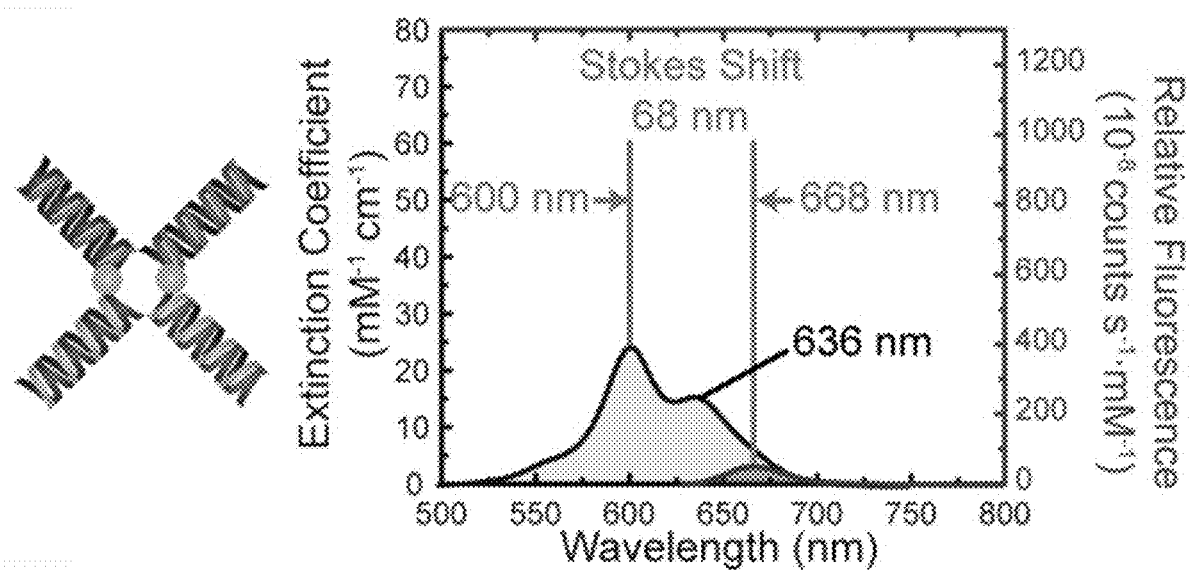
FIG. 6E is the fluorescence spectra of a 4AJ templated Cy5 transverse dimer.
Figure 6F:
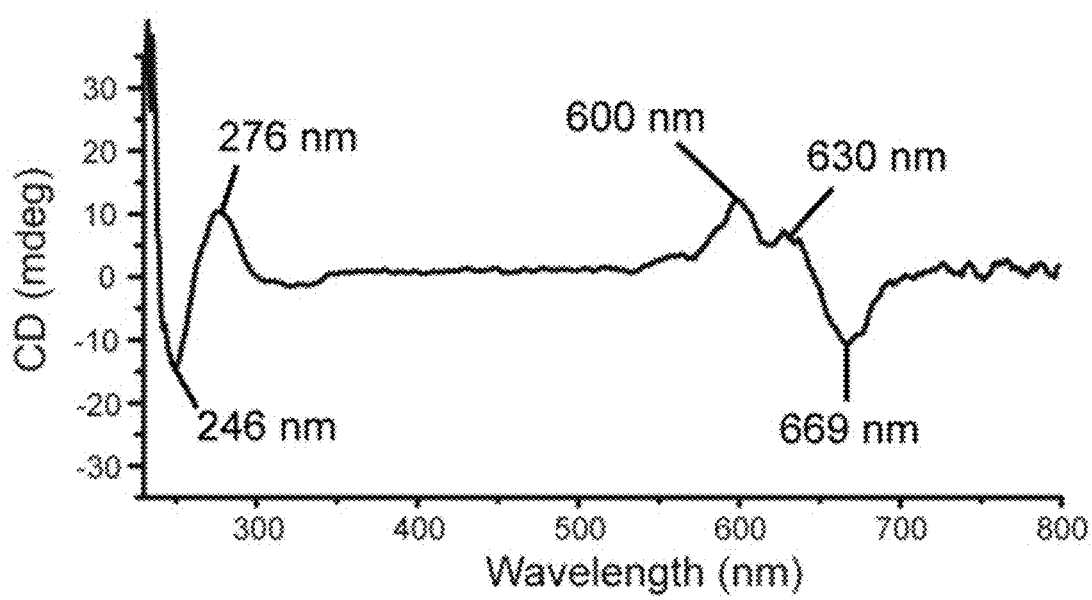
FIG. 6F is the CD of a 4AJ templated Cy5 traverse dimer.
Figure 6G:
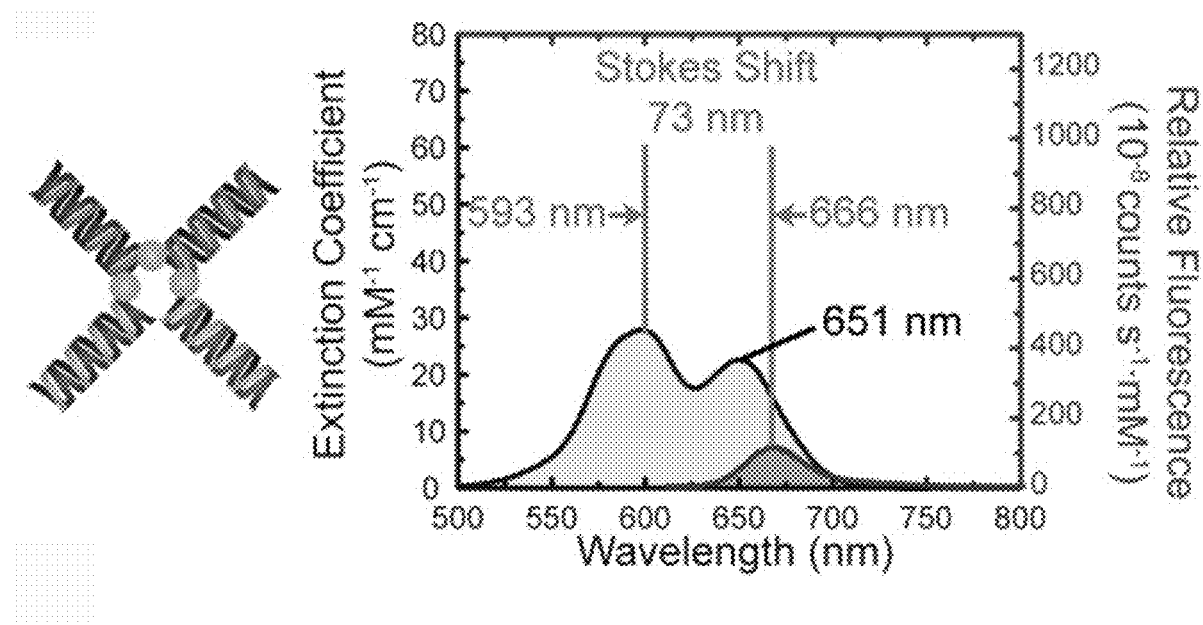
FIG. 6G is the fluorescence spectra of a 4AJ templated Cy5 trimer.
Figure 6H:
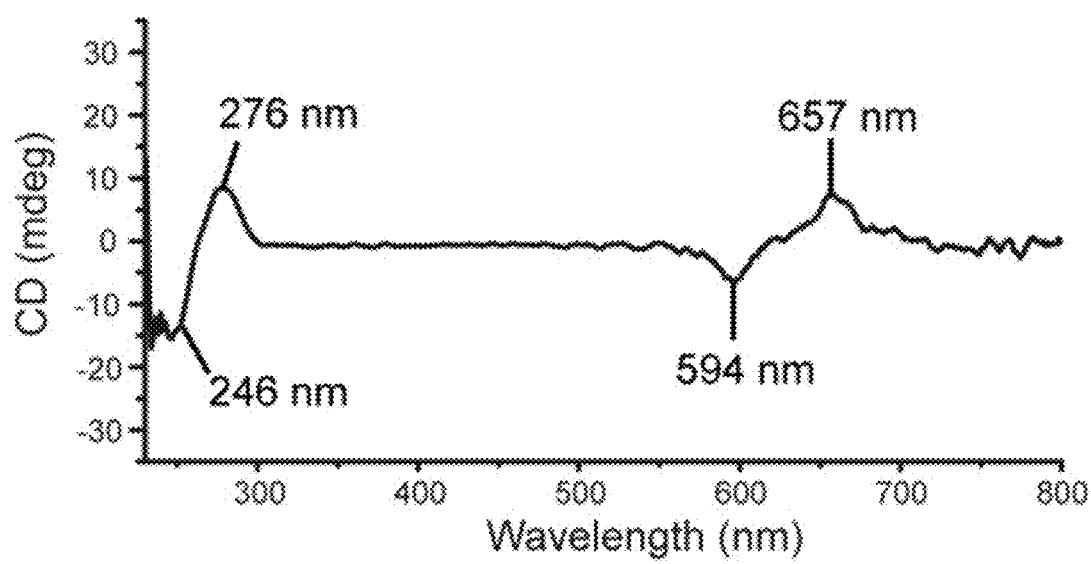
FIG. 6H is the CD of a 4AJ templated Cy5 trimer.
Figure 6I:
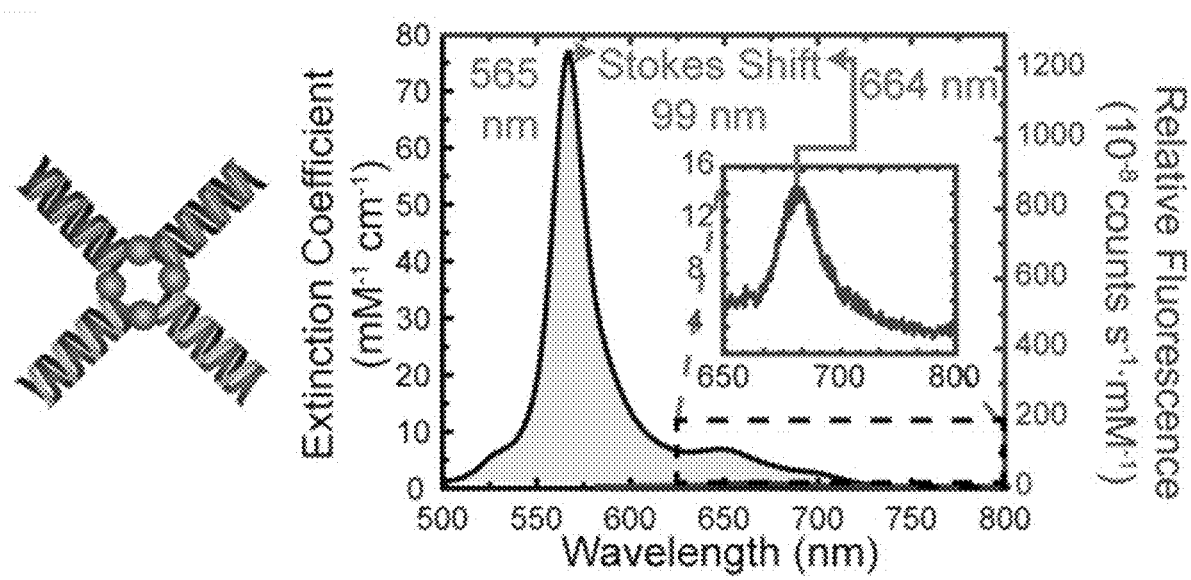
FIG. 6I is the fluorescence spectra of a 4AJ templated Cy5 tetramer.
Figure 6J:
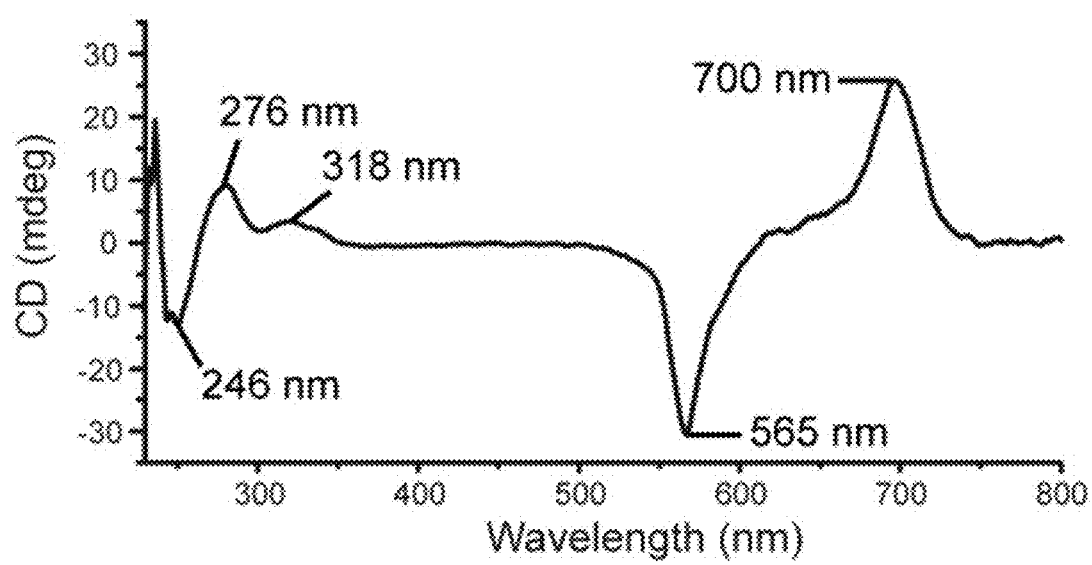
FIG. 6J is the CD of a 4AJ templated Cy5 tetramer. All samples were prepared at 10 μM DNA concentrations in 1×TAE buffer solution with 15 mM $MgCl_2$ added.

To further determine the characteristics of chromophores attached to a nucleotide template in a immobile 4AJ architecture, Cy5 chromophores were attached as a monomer (FIG. 6A), a dimer where the monomers are adjacent to each other (FIG. 6B), a dimer where the monomers are opposite of each other (FIG. 6C), a timer (FIG. 6D), and a tetramer (FIG. 6E) (see Cannon et al., 2018, Supplemental Information). Absorbance and circular dichroism (CD) was then measured. All measurements were performed with the architectures in a solution of 10 µM DNA, 1×TAE buffer with 15 mM $MgCl_2$.

The monomer reveled a single absorbance and emission peak maxima at 653 and 666 nm respectively. Although the monomer absorbance peak maximum is slightly red-shifted from the literature value, the shift is most likely due to increased rigidity of the 4AJ structure, chromophore-DNA interactions, and surrounding base sequences. As expected, the dye monomer did not produce a CD signal within the visible range, indicating the absence of molecular chirality and excitonic coupling. Likewise, the CD signals appearing in the UV range at 246 and 276 nm, respectively, result from the expected right-handed macromolecular structure of the β-DNA helix.

The adjacent dimer shows predominantly J-type aggregate behavior, with an absorbance peak maximum at 662 nm that is slightly red-shifted relative to the monomer. This red-shift in absorbance yields a small Stokes shift of 5 nm, which is near resonance florescence behavior. A second, smaller absorbance peak also appears at 602 nm. The appearance of the two peaks is indicative of a Davydov splitting of 58 nm. The adjacent dimer exhibits a split CD signal at 600 and 675 nm. The ± of the CD peaks signifies right-handed chirality and is anticipated owing to the right-handed nature of the DNA helix. Because of the predominant J-type behavior and presence of Davydov splitting and CD signal, the chromophores are most likely arranged head-to-tail with some break in planarity between the molecules, or oblique-like arrangement, that favors J-aggregate stacking.

In contrast, the transverse dimer shows optical behavior that is roughly opposite that of the adjacent dimer. The primary absorbance peak is blue-shifted, with an absorbance maximum at 600 nm and a much smaller red-shifted absorbance peak at 636 nm, corresponding to an even smaller 36 nm Davydov splitting. A 68 nm Stokes shift is observed when comparing the primary absorbance peak to the fluorescence peak at 668 nm, which is much reduced in intensity, about 97.6%. The blue-shifted primary absorbance peak, the large Stokes shift, and the reduced fluorescence intensity are all indicative of predominantly H-type aggregate behavior. The small Davydov splitting and a relatively strong ∓CD signal at 600 and 669 nm, respectively, of the transverse dimer indicates left-handed chirality and an oblique stacking arrangement that does not stack in a perfectly parallel or H-type arrangement. A small absorbance peak at 630 and 669 nm shows excitonic coupling between the chromophores. The considerably decreased fluorescence emission is indicative of fluorescence suppression due to a forbidden optically transition.

The trimer shows absorbance and fluorescence properties similar to the transverse dimer. Most notably, the trimer absorbance spectrum shows an absorbance peak at 593 nm that is blue-shifted from the monomer by 60 nm and a smaller peak at 651 nm that is slightly blue-shifted by 2 nm. The absorbance spectrum also reveals broadening of the primary peak by 15 nm compared to the monomer, as indicated by an increase in the full-width at half-maximum value. Without being bound to a particular theory, the broadening mostly likely arises from a distribution of trimer dye configurations (i.e., dye positions and orientations). In combination with the blue-shifted absorbance peak, the timer shows about an 85% suppression of the fluorescence emission intensity relative to the monomer, indicative of net H-aggregate behavior. Similar to the other aggregate configurations, the trimer has an observed excitonically coupled circular dichroism (EC-CD) signal that, though small, indicates a slightly imperfect stacking arrangement with minor obliqueness. Additionally, the aggregate displays right-handedness, like the adjacent dimer.

The tetramer dye aggregate configuration produces the most interesting optical spectra. A large Davydov splitting of 125 nm (397.5 meV), extensive enough to induce a visible color change in the solution, was observed. This is the largest reported splitting for DNA templated dye aggregates. The Davydov splitting is characterized by a significantly blue-shifted intense absorbance peak at 565 nm and a red-shifted much less intense peak at 690 nm. Though difficult to resolve in the absorption spectrum, the absorbance peak at 690 nm is further substantiated by a large signal in the CD spectrum at 700 nm. Note that the difference in extinction coefficients of the various dye aggregates result from two key effects: (1) the differences in dye number and (2) exciton delocalization and exciton-vibrational interactions. The tetramer also exhibits strong fluorescence suppression behavior at 664 nm, with a 97.6% decrease in the fluorescent emission relative to the monomer, as determined by peak area. The large Davydov splitting, strong fluorescence suppression, and 99 nm Stokes shift provide solid evidence of a dye assembly with predominantly H-type stacking. The pronounced ∓CD signal of the tetramer configuration indicates strong exciton coupling between the dyes and reveals that the dyes are oriented predominantly in a parallel manner with some obliqueness that is supported by the absorbance peak at 690 nm. Comparing the optical spectra of the immobile 4AJ-templated tetramer presented here with the mobile 4AJ-templated tetramer observed in our prior study, the most notable difference is in the CD spectrum. Interestingly, the immobile tetramer shows right-handedness, while the mobile tetramer shows left-handedness. Additionally, an absorbance peak at 665 nm was observed for the mobile 4AJ-templated tetramer. In contrast, for the immobile tetramer, a very subtle peak was observed for at 690 nm that was further supported by a strong CD signal, indicating obliqueness within the immobile tetramer. These differences are most likely due to the base-pair stacking of the immobile tetramer locking the aggregate core such that the DNA junction does not undergo restacking. The mobile tetramer undergoes DNA breathing and base-pair restacking and was found to partition into two J-dimer pairs that are displaced either horizontally or vertically along the arms, which accounts for the observed 665 nm absorbance peak.

Therefore, each of the different arrangements shows unique absorbance and emittance properties that may be leveraged in the different embodiments.

Example 6

To test the effect strand invasion has on absorption of the various structures, both a linear, double stranded DNA architecture with a Cy5 dimer (FIG. 7) and a 4AJ architecture with a Cy5 tetramer (FIG. 10) were assayed.

As shown in FIG. 7, in a solution of 4.5 µM DNA in 1×TAE with 15 mM $MgCl_2$, the absorption at 563 nm versus time shows a large increase in absorption as the two single stranded nucleotide oligomers pair. This change in absorption is lost when an invasion strand causes the dimer to separate back into two monomers. The change in absorbance, due to the Davydov splitting, is so great that it causes a change in the visible color of the solution.

Figure 10A:
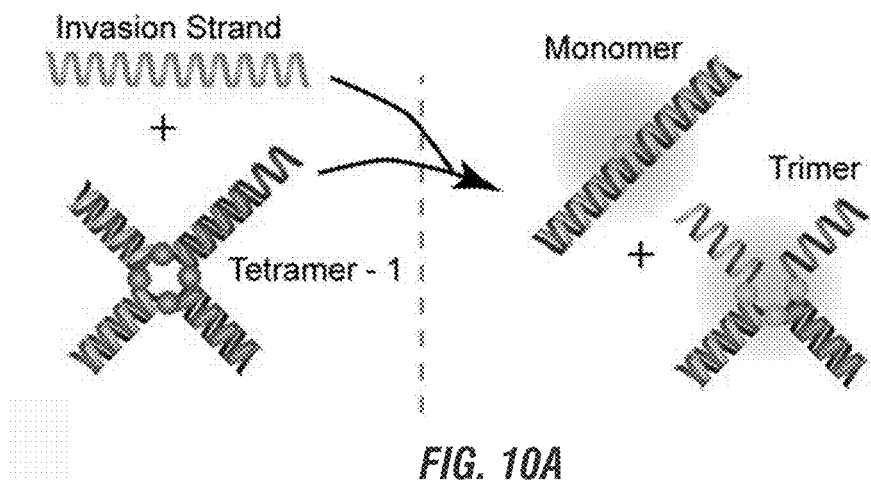
FIG. 10A is a schematic representation of an optical reporter in which the invasion strand binding to a toehold of a 4-arm junction (4AJ) causing the tetramer with nearly zero fluorescence while assembled, disassociating into a monomer and a trimer.

Additionally, as shown in FIG. 10A, a 4AJ with a 10-nucleotide toehold domain on one of the four arms allowed for an invasion strand to separate the tetramer into a monomer and trimer. Upon invasion, the coherent excitonic delocalization within the aggregate would cease and greatly increased fluorescence would ensue from the chromophores on both the monomer and the trimer. The operation of the fluorescence scheme yielded a 25-fold increase in fluorescence intensity upon disassembly of the 4AJ into a monomer and trimer.

Figure 10B:
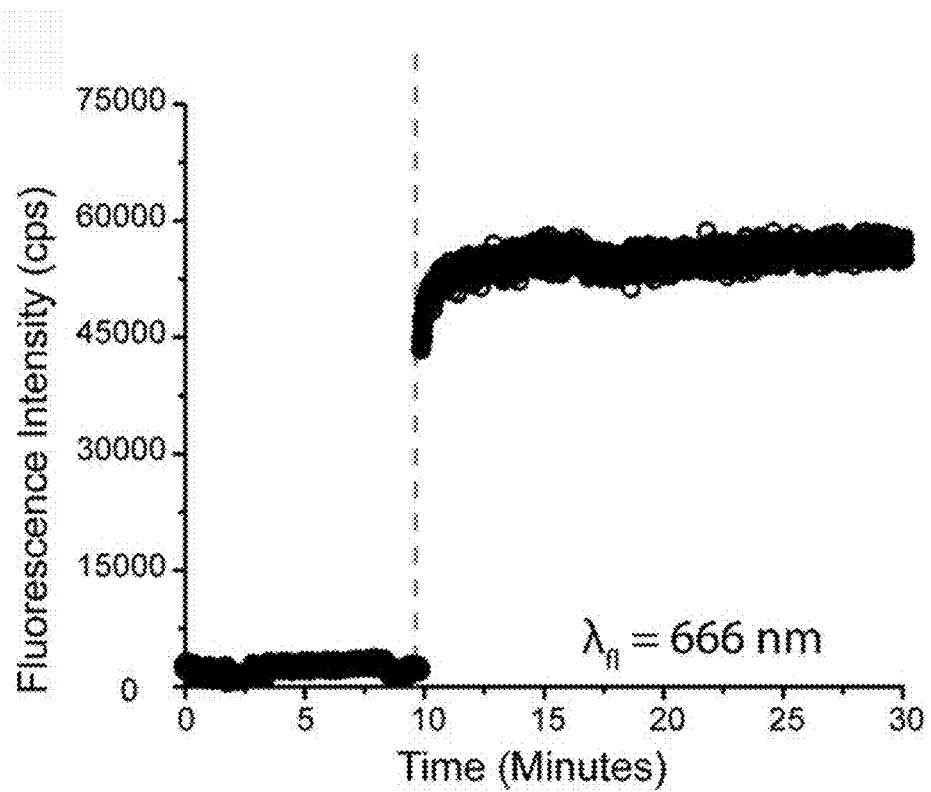
FIG. 10B is a graphical representation showing an increase in fluorescence intensity upon disassembly of the 4AJ.
Figure 10C:
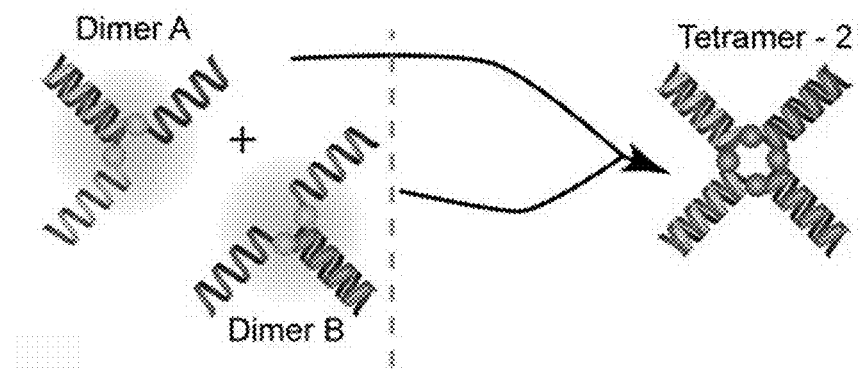
FIG. 10C is a schematic representation of two dimer chromophores with minimal absorption self-assembling into a full tetramer in a 4AJ architecture.
Figure 10D:
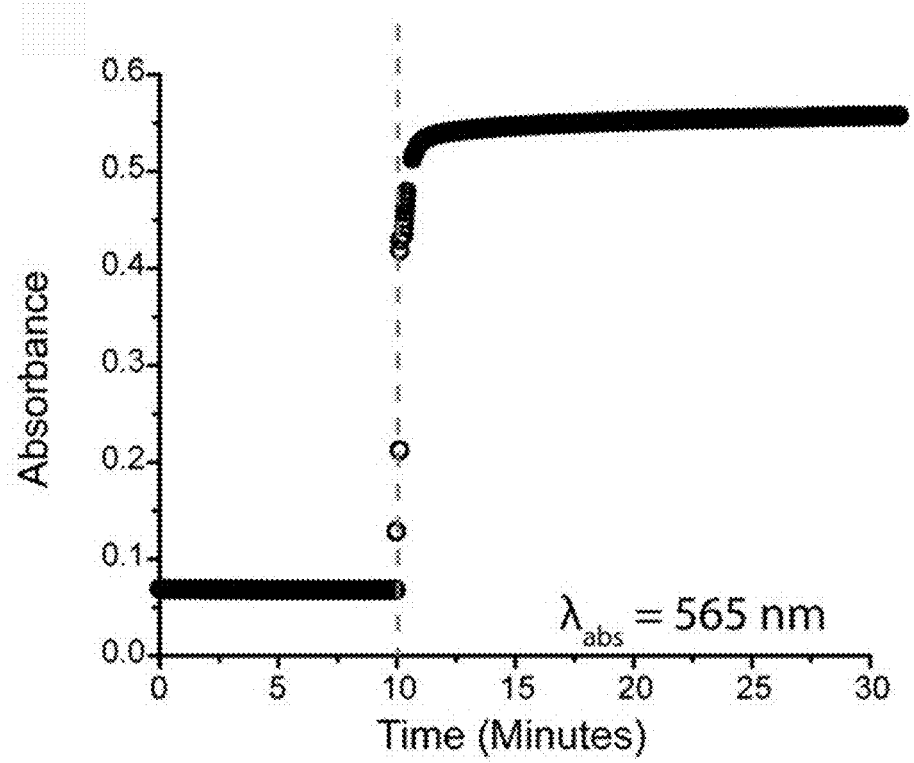
FIG. 10D is the graphical representation showing the increase in absorbance upon assembly into of the full tetramer.

Conversely, as shown in in FIG. 10B, two halves of the 4AJ were hybridized in solution together to form a full 4AJ. While separate, the dimer exhibited minimal absorbance at 565 nm (the H-tetramer absorbance peak), yielded a cyan solution color. When assembled, the absorption of the complete 4AJ at 565 nm greatly increases, yielding a solution color change to violet. The absorbance reaction gave a 10-fold increase in absorbance at 565 nm.

Therefore, both the linear and 4AJ architectures will act as highly sensitive optical reporters.

Example 7

Figure 11A:
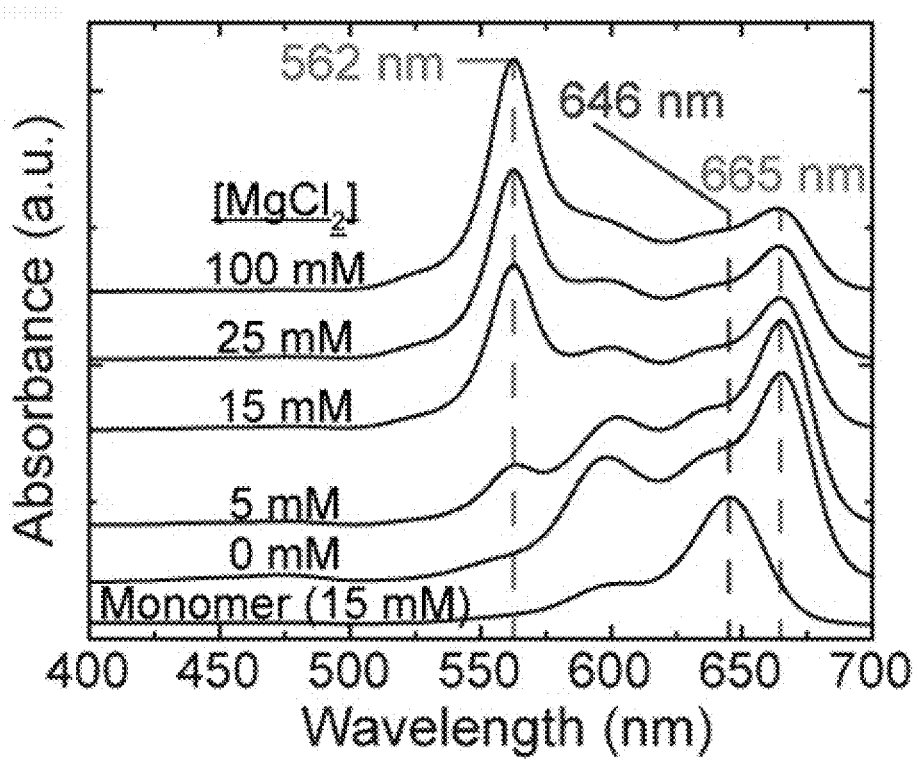
FIG. 11A is a graphical representation of the absorbance spectra of Cy5 J-dimers and/or H-tetramers bound to a mobile 4-arm junction template with varied $MgCl_2$ with a constant DNA concentration.
Figure 11B:
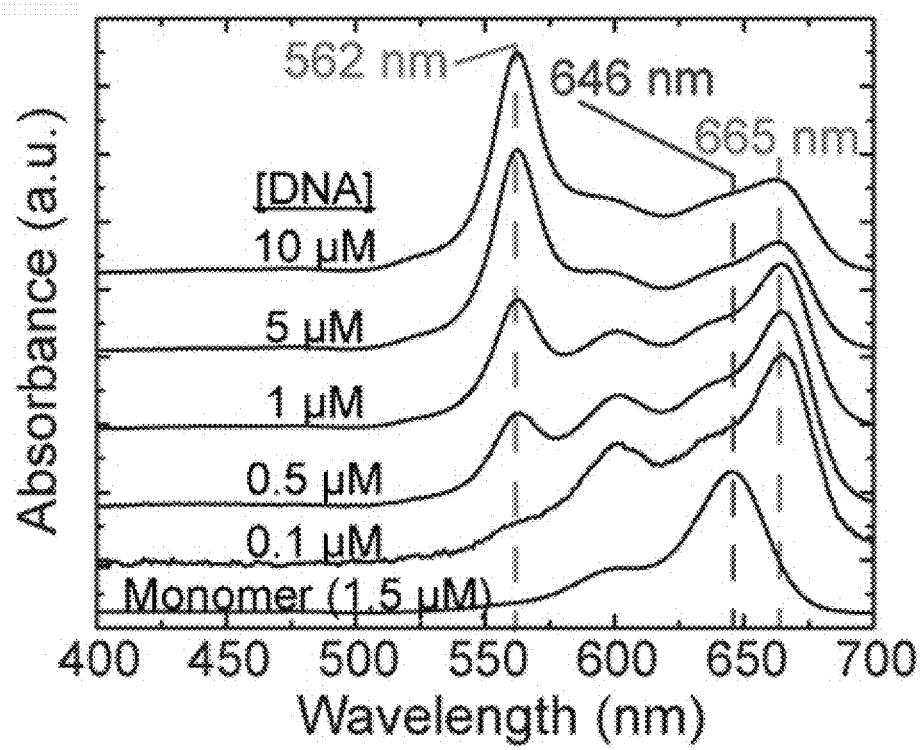
FIG. 11B is a graphical representation of the absorbance spectra of Cy5 J-dimers and/or H-tetramers bound to a mobile 4-arm junction template with varied DNA with a constant $MgCl_2$ concentration.
Figure 12A:
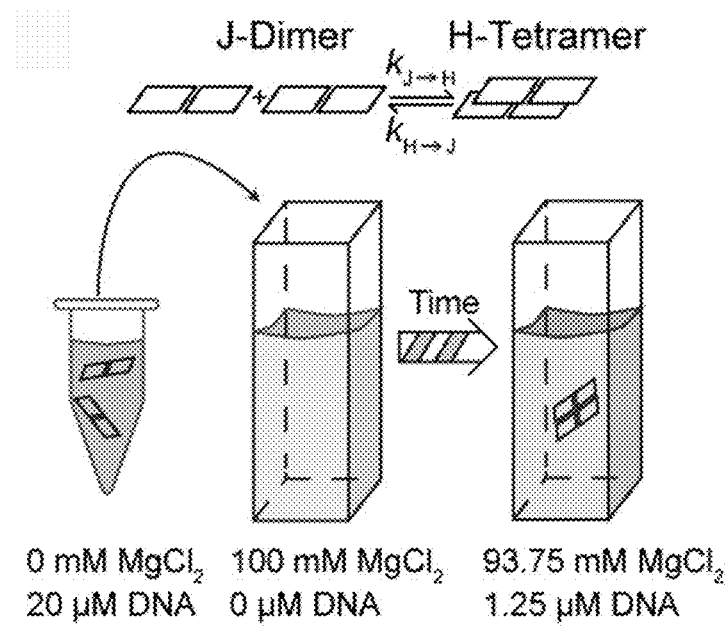
FIG. 12A is a schematic representation of the changes of J-dimers in a low salt concentration solution into H-tetramers in a high salt solution on mobile 4-arm junctions over time due to four-way branch migration.
Figure 12B:
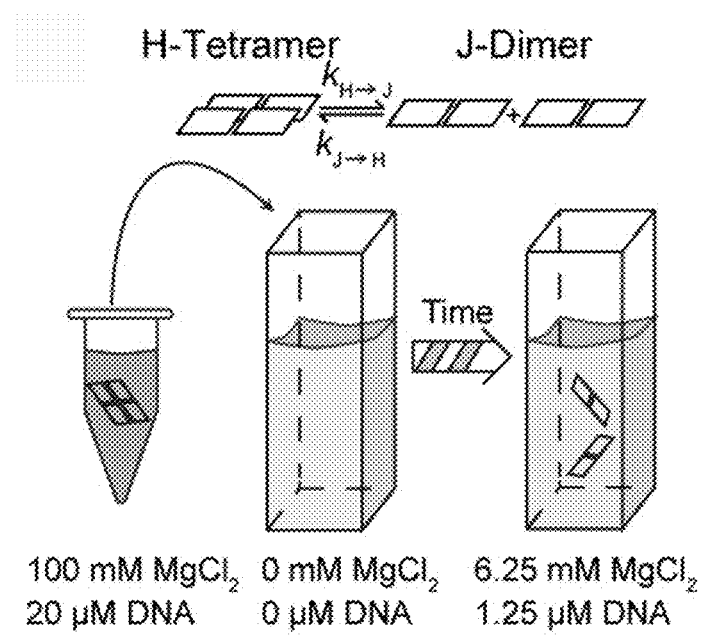
FIG. 12B is a schematic representation of the changes of H-tetramers in a high salt solution into J-dimers in a solution without salt over time due to disassociation of the complement sequences of the mobile 4-arm junction.

To further characterize environmental effect on more complex structures of a mobile nucleotide template, Cy5 chromophores were attached to four different ssDNA strands (see Cannon et al., *Coherent Exciton Delocalization in a Two-State DNA-Templated Dye Aggregate System*, 2017, J. Phys. Chem. A, 121:6905-6916, Supplemental Information, herein incorporated by reference) and solution salt and DNA concentrations were varied. The four different ssDNA strands were designed to allow two complement ssDNA strands to form two dsDNA strands. The two dsDNA strands may then undergo four-way branch migration to form a 4AJ template. The complementary ssDNA strands were first annealed to position the Cy5 chromophores into a J-dimer. The Cy5 chromophore were further positioned such that if the two dsDNA strands form the 4AJ template, the resulting Cy5 tetramer would form H-dimers. The two dsDNA strands were then mixed at various salt (0-100 mM added MgCl2; DNA held constant at 1.5 µM) and DNA (0.1-10 µM; salt held constant at 15 mM) concentrations. The absorbance spectrum of each sample (FIGS. 11A and 11B) at various salt and DNA concentrations was measured. FIGS. 11A and 11B shows that with changes in salt or DNA concentration the locations of the absorbance peaks remain constant within the selected $MgCl_2$ and DNA concentration ranges, respectively.

The absence of variation in the position of the absorption peaks shows that the relative orientations between the two dyes are constant for the two populations, showing that the dyes do not continuously rearrange their configuration as a function of salt concentration or DNA concentration but instead exist in one of two geometrically distinct states, as a J-dimer (duplex) or an H-tetramer (4AJ). Accordingly, the relative concentration of each aggregate state varies with salt concentration and/or DNA concentration as indicated by the change in relative peak intensities for the J-dimer ($\lambda_{max}$=665 nm) and the H-tetramer ($\lambda_{max}$=562 nm). The increase of intensity at 562 nm for both the increase in salt and DNA show that at higher concentrations of both salt and DNA, the H-tetramer is favored over the J-dimers (FIGS. 11A, 11B, 12A and 12B). Thus, the observed spectra are a manifestation of spectral overlap between J- and H-aggregates.

This shows that the intensity of absorbance may be controlled of mobile templates by altering the salt and/or DNA concentrations. This further shows that depending on the rigidity of the DNA architecture, salt and/or DNA concentrations may be altered in order to fine tune the absorbance spectra.

What is claimed is:

1. A method of detecting a target involving a near-field absorption coupling for colorimetric detection, comprising:
    changing a proximity of a first chromophore bound to the first nucleotide architecture to a second chromophore bound to a second nucleotide architecture, wherein the first and second nucleotide architectures are mobile or flexible;
    binding a targeting molecule to the one or more nucleotide oligomers to form the first and second nucleotide architectures;
    changing the orientation of the first chromophore to the second chromophore;
    producing a color change in an absorbance spectrum of the first chromophore or the second chromophore;
    bringing said second chromophore sufficiently close to said first chromophore;
    creating the near-field interference such that the first and second chromophores act as one chromophore;
    electronically coupling the first chromophore to the second chromophore to create a delocalized exciton; and
    utilizing the delocalized exciton to process quantum information with a colorimetric detection system or a circuit;
    wherein the colorimetric detection or the circuit detects a complement strand in a sample using the targeting molecule.

2. The method of claim 1, further comprising separating said second chromophore and said first chromophore from the one chromophore.

3. The method of claim 1, further comprising selecting the first chromophore or the second chromophore from the group consisting of 6-FAM, Fluorescein dT, Cy3, TAMRA, JOE, Cy5, TAMRA, MAX, TET, Cy5.5, ROX, TYE 563, Yakima Yellow, HEX, TEX 615, TYE 665, TYE 705, Alexa Fluor 488, 532, 546, 647, 660, 750, 5' IRDye 700, 800, and 800CW, ATTO™ 488, 532, 550, 565, Rho101, 590, 633, 647N, Rhodamine Green-X, Rhodamine Red-X, 5-TAMRA, WellRED D4, D3, and D2, 6-FAM, Fluorescein, Texas Red-X, Lightcycler 640, Dy-530, -547, -547P1, -548, -549, -549P1, -550, -554, -555, -556, -560, -590, -591, -594, -605, -610, -615, -630, -631, -632, -633, -634, -635, -636, -647, -647P1, -648, -648P1, -649, -649P1, -650, -651, -652, -654, -675, -676, -677, -678, -679P1, -680, -681, -682, -700, -701, -703, -704, -705, 730, -731, -732, -734, -749, -749P1, -750, -751, -752, 754, -756, -757, -758, -780, -781, -782, -800, -831, -480XL, -481XL, -485XL, -510XL, -511XL, -520XL, -521XL, and -601XL.

4. The method of claim 1, wherein the one or more nucleotide oligomers are selected from the group consisting of: RNA, DNA, LNA, PNA, and UNA.

5. The method of claim 4 further comprising forming a four-arm junction architecture with four DNA bricks from the one or more nucleotide oligomers.

6. The method of claim 5 further comprising detecting a target with one of the four DNA bricks.

7. The method of claim 6 further comprising disassociating a targeting DNA brick from the four-arm junction architecture.

8. The method of claim 7 further comprising forming a tetramer with the first chromophore and the second chromophore.

9. The method of claim 8 wherein each monomer of the tetramer is bound to separate DNA bricks of the four DNA bricks.

10. The method of claim 8 further comprising disassociating the tetramer into a monomer and a trimer when the targeting DNA brick dissociates from the four-arm junction architecture.

11. The method of claim 1 further comprising:
    binding a first nucleotide oligomer of the one or more nucleotide oligomers to the first chromophore; and
    binding a second nucleotide oligomer of the one or more nucleotide oligomers to the second chromophore.

12. The method of claim 11 wherein the first nucleotide oligomer and the second nucleotide oligomer have different targets.

13. The method of claim 12 further comprising:
    forming a first DNA targeting brick and a second targeting DNA brick with the one or more oligomers,
    wherein the first chromophore is bound to the first targeting DNA brick and the second nucleotide oligomer is bound to the second targeting DNA brick.

14. The method of claim 13 further comprising forming a scaffold with the one or more oligomers.

15. The method of claim 14 further comprising:
binding a third chromophore and a fourth chromophore to the scaffold;
forming a first dimer with the first chromophore and the third chromophore;
forming a second dimer with the second chromophore and the fourth chromophore.

16. The method of claim 15 further comprising:
dissociating the first dimer when the first targeting DNA brick detects a first target; and
dissociating the second dimer when the second targeting DNA brick detects a second target.

17. The method of claim 15 further comprising recombining the delocalized exciton with an interaction energy that differs from an exciton of the third chromophore, wherein the fourth chromophore has a similar absorption-emission behavior to the recombined exciton of the first and second chromophores.

18. The method of claim 1 further comprising transferring the delocalized exciton from the first chromophore to the second chromophore.

\* \* \* \* \*